United States Patent [19]

Goto et al.

[11] Patent Number: 4,804,665

[45] Date of Patent: Feb. 14, 1989

[54] AZASPIRO COMPOUNDS AND THEIR USE

[75] Inventors: Giichi Goto, Toyono; Akinobu Nagaoka, Kawanishi, both of Japan

[73] Assignee: Takeda Chemical Industries, Ltd., Osaka, Japan

[21] Appl. No.: 137,713

[22] Filed: Dec. 24, 1987

[30] Foreign Application Priority Data

Dec. 27, 1986 [JP] Japan ................................ 61-313381
Nov. 10, 1987 [JP] Japan ................................ 62-283396

[51] Int. Cl.[4] .................. C07D 471/10; A61K 31/395
[52] U.S. Cl. ........................................ 514/278; 546/16
[58] Field of Search ........................... 546/16; 514/278

[56] References Cited

U.S. PATENT DOCUMENTS 3,635,991 1/1972 Archer ................................. 540/16

FOREIGN PATENT DOCUMENTS 1211646 3/1966 Fed. Rep. of Germany ........ 540/16
167691 7/1986 Japan ..................................... 546/16
2142332 1/1985 United Kingdom .................. 546/16

OTHER PUBLICATIONS

Bolliger et al., Chem. Abstracts 106; 188459r (1987).
Mukai et al., Chem. Abstracts 76: 14367f (1972).
McElvain et al., J. Am. Chem. Soc., vol. 72, pp. 384–389 (1950).
Noring et al., Psychopharmacology (1984) 84:569–571.
Wettstein et al., Psychopharmacology (1984) 84:572–573.

*Primary Examiner*—Robert T. Bond
*Attorney, Agent, or Firm*—Wenderoth, Lind & Ponack

[57] ABSTRACT

Azaspiro compounds of the formula

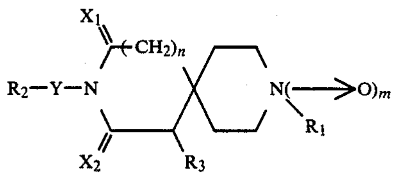

wherein $R_1$ and $R_2$ independently represent hydrogen, a hydrocarbon residue which may have a substituent, or an acyl group which may have a substituent; $R_3$ represents hydrogen or a hydrocarbon residue which may have a substituent; each of $X_1$ and $X_2$ is oxygen or sulfur; Y represents oxygen, sulfur or a group of the formula: $-N(R_4)-$, wherein $R_4$ represents hydrogen or a lower alkyl group; m represents 0 or 1; n represents 0 or 1, and its salt are novel compounds, possess excellent brain function-improving action, and are of use as drugs for the prevention and therapy of senile dementia of Alzheimer type, vascular-type dementia and dementia derived from Alzheimer's disease, Pick's disease, Huntington's disease, Creutzfeldt-Jakob's disease, Parkinson's disease and spinocerebellar degeneration.

15 Claims, No Drawings

AZASPIRO COMPOUNDS AND THEIR USE

FIELD OF INDUSTRIAL APPLICATION

The present invention relates to a novel azaspiro compound that is useful as a pharmaceutical, specifically as a brain function-improving drug for senile dementia, Alzheimer's disease, etc.

PRIOR ART

In the trend toward an aged society, various compounds possessing brain function-improving activity have been proposed. Arts relating to some azaspiro compounds have been published (Japanese Published Unexamined Patent Application No. 36487/1985, Japanese Published Unexamined Patent Application No. 167691/1986).

PROBLEM TO BE SOLVED BY THE INVENTION

With the above mentioned social problem as background, drugs which act on the central nervous system, specifically those which may be designated as brain function-improving drugs for senile dementia and Alzheimer's disease are highly sought after, but no satisfactory compound has yet been found.

MEANS OF SOLVING THE PROBLEMS

The present inventors attempted to find a compound useful as a brain function-improving drug which acts on the central nervous system, specifically the acetylcholine receptor; it was found that an azaspiro compound of the formula:

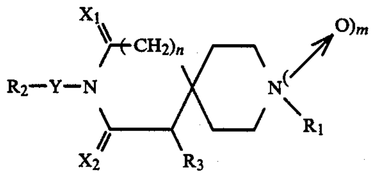

(I)

wherein $R_1$ and $R_2$ independently represent hydrogen, a hydrocarbon residue which may have a substituent, or an acyl group which may have a substituent; $R_3$ represents hydrogen or a hydrocarbon residue which may have a substituent; each of $X_1$ and $X_2$ is oxygen or sulfur; Y represents oxygen, sulfur or a group of the formula: —N($R_4$)—, wherein $R_4$ represents hydrogen or a lower alkyl group having 1 to 4 carbon atoms; m represents 0 or 1; n represents 0 or 1, and its salt both exhibit excellent brain function-improving action, and developed the present invention.

As examples of hydrocarbon residues for the "hydrocarbon residue which may have a substituent" represented by $R_1$, $R_2$ and $R_3$ in the above formula (I), mention may be made of chain, cyclic, saturated and unsaturated aliphatic hydrocarbon residues and various combinations thereof.

As examples of saturated aliphatic hydrocarbon residues, mention may be made of straight-chain and branched alkyl groups with 1 to 6 carbon atoms (e.g., methyl, ethyl, n-propyl, isopropyl, n-butyl, isobutyl, tert-butyl, n-pentyl and n-hexyl).

As examples of unsaturated aliphatic hydrocarbon residues, mention may be made of straight-chain and branched ($C_{2-4}$)alkenyls (e.g., vinyl, allyl and 2-butenyl) and ($C_{2-4}$)alkynyls (e.g., propargyl and 2-butynyl).

As examples of cyclic saturated hydrocarbon residues, mention may be made of monocyclic cycloalkyls with 3 to 7 carbon atoms (e.g., cyclobutyl, cyclopentyl, and cyclohexyl) and bridged cyclic saturated hydrocarbons with 8 to 14 carbon atoms (e.g., bicyclo[3,2,1]oct-2-yl and bicyclo[3,3,1]nonan-2-yl); as examples of cyclic unsaturated hydrocarbon residues, mention may be made of phenyl and naphthyl groups.

As examples of substituents for these hydrocarbon residues, mention may be made of halogen atoms (e.g., chlorine, bromine, and iodine), nitro, cyano, hydroxy, ($C_{1-4}$)alkoxys (e.g., methyloxy, ethyloxy, propyloxy, butyloxy and isopropyloxy), ($C_{1-4}$)alkylthios, (e.g., methylthio, ethylthio, propylthio, isopropylthio and butylthio), amino, mono- or di($C_{1-4}$)alkyl-substituted aminos (e.g., methylamino, ethylamino, propylamino, dimethylamino and diethylamino), mono- or di-aralkyl-substituted amino (e.g. benzylamino, 2-hyroxyphenylmethylamino), mono- or di-pyridylcarbonyl-substituted amino (e.g. 3-pyridylcarbonylamino), ($C_{1-4}$)alkoxycarbonyls (e.g., methoxycarbonyl, ethoxycarbonyl, propoxycarbonyl and isobutoxycarbonyl), hydroxycarbonyl, ($C_{1-6}$)alkylcarbonyls (e.g., methylcarbonyl, ethylcarbonyl and butylcarbonyl), ($C_{3-6}$)cycloalkylcarbonyl (e.g. cyclohexylcarbonyl, cyclopentylcarbonyl), carbamoyl, mono- or di($C_{1-4}$)alkyl-substituted carbamoyls (e.g., methylcarbamoyl, ethylcarbamoyl, propylcarbamoyl, butylcarbamoyl, diethylcarbamoyl and dibutylcarbamoyl) phenyl, phenoxy, benzoyl, phenoxycarbonyl, phenyl($C_{1-4}$)alkyl-carbamoyl (e.g. benzylcarbamoyl, phenethylcarbamoyl) and phenylcarbamoyl, all of which may have 1 to 4 substituent [As examples of substituents for each phenyl group, mention may be made of ($C_{1-4}$)alkyl groups (e.g. methyl, ethyl, propyl, butyl and isopropyl), halogens (e.g. chlorine, bromine and iodine), hydroxyl, benzyloxy, amino, mono- or di-($C_{1-4}$)alkyl-substituted aminos (e.g. methylamino, ethylamino, propylamino, dimethylamino, diethylamino, methylethylamino), nitro, and ($C_{1-4}$)alkoxycarbonyls (e.g. methoxycarbonyl, ethoxycarbonyl, propoxycarbonyl).].

It is appropriate that the substituents for these hydrocarbon residues number 1 to 3.

As examples of acyl groups represented by $R_1$ and $R_2$ mention may be made of carboxylic acyls, carbamic acyls, sulfonic acyls and substituted oxycarbonyl, all of which may have a substituent. When the acyls have a substituent or substituents, the substituents of the hydrocarbon residue shown above are mentioned as the substituents of the acyls.

As examples of carboxylic acyls, mention may be made of ($C_{1-6}$)alkylcarbonyls such as acetyl, propionyl, butyryl, valeryl, hexanoyl, isobutyryl and isovaleryl. (These may be substituted by amino, 3-carbamoyl-1,4-dihydropyridin-1-yl, 3-carbonyl-1-pyridyl, phenoxy, etc.) As examples of $C_{1-6}$ alkylcarbonyl substituted, mention may be made of phenoxyacetyl, 4-aminobutyryl, aminomethylcarbonyl, 2-(3-carbamoyl-1,4-dihydropyridin-1-yl)ethylcarbomoyl, 2-(3-carbamoylpyridin-1-yl)ethylcarbonyl); ($C_{3-8}$)cycloalkyl-carbonyls such as cyclopentylcarbonyl and cyclohexylcarbonyl; ($C_{3-8}$)cycloalkyl-($C_{1-6}$)alkylcarbonyls such as cyclopentylacetyl; ($C_{2-6}$) alkenyl- or alkynylcarbonyls such as acryloyl, crotonyl, 2-pentenoyl, 4-pentinoyl, 2-hexenoyl, 3-hexenoyl and 2,4-hexadienoyl; arylcarbonyls such as benzyl and naphthoyl; pyridylcarbonyls such as nicotinoyl; dihydropyridylcarbonyls [These may be substituted by ($C_{1-4}$) alkyl (e.g. methyl, ethyl, propyl, butyl), benzyl, methoxycarbonyl, 3-nitrophenyl, nitro, 2-trifluorophenyl, etc. As examples of dihydropyridylcarbonyl, mention may be made of N-($C_{1-4}$)alkyl-1,4-dihidropyridine-3-carbonyl (e.g. N-methyl-1,4-dihydropyridine-3-carbonyl, N-ethyl-1,4-dihidropyridine-3-carbonyl, N-butyl-1,4-dihidropyridine-3-carbonyl), N-benzyl-1,4-dihydropyridine-3-carbonyl, 2,6-dimethyl-5-methoxycarbonyl-4-(3-nitrophenyl)-1,4-dihydropyridin-3-ylcarbonyl, 2,6-dimethyl-5-nitro-4-(2-trifluorophenyl-1,4-dihydropyridin-3-ylcarbonyl)]; and pyridiniumcarbonyl. [This is a pyridine substituted at nitrogen by $C_{1-4}$ alkyl (e.g. methyl, ethyl), benzyl, etc. As the examples of pyridiniumcarbonyl, mention may be made of alkylpyridinum-3-carbonyl (e.g. methylpyridinium-3-carbonyl, ethylpyridinium-3-carbonyl) and benzylpyridinium-3-carbonyl)].

As examples of carbamic acyls mention may be made of carbamoyl and mono- or di-substituted carbamoyls. As examples of such mono-, or di-substituted carbamoyls, mention may be made of mono- or di($C_{1-4}$) alkylcarbamoyls such as methylcarbamoyl, ethylcarbamoyl, propylcarbamoyl, butylcarbamoyl, dimethylcarbamoyl, diethylcarbamoyl and dipropylcarbamoyl; mono- or di($C_{3-6}$)alkenyl- or alkynylcarbamoyls such as allylcarbamoyl, 3-butenylcarbamoyl, 4-pentenylcarbamoyl and diallylcarbamoyl; and aromatic group carbamoyls such as phenylcarbamoyl, naphthylcarbamoyl and diphenylcarbamoyl.

As examples of sulfonic acyls, mention may be made of inorganic sulfonyl group such as sodium sulfonyl; ($C_{1-6}$)alkyl-sulfonyls such as methylsulfonyl, ethylsulfonyl, propylsulfonyl and butylsulfonyl; ($C_{2-6}$)alkenyl- or alkynylsulfonyls such as allylsulfonyl and 2-methyl-2-propanesulfonyl; and aromatic sulfonyls such as phenylsulfonyl and naphthalenesulfonyl.

As examples of substituted oxycarbonyl, mention may be made of ($C_{1-6}$)alkyloxycarbonyls unsubstituted or substituted by a halogen (e.g. fluorine, chlorine, bromine, iodine, etc.), cyano, benzyloxy, phenoxy, di-($C_{1-3}$)alkylamino (e.g. dimethylamino, diethylamino, dipropylamino), ($C_{1-4}$)alkyloxy (e.g. methyloxy, ethyloxy, butyloxy, t-butyloxy), ($C_{1-3}$)alkylthio (e.g. methylthio, ethylthio, propylthio), 4-(3-nitrophenyl)-2,6-dimethyl-3-methoxycarbonyl-1,4-dihydropyridine-5-ylcarbonylamino and dihydropyridylcarbonylamino (e.g. methyloxycarbonyl, ethyloxycarbonyl, n-propyloxycarbonyl, i-propyloxycarbonyl, n-butyloxycarbonyl, sec.-butyloxycarbonyl, tert.-butyloxycarbonyl, n-hexyloxycarbonyl, 2-fluoroethyloxycarbonyl, 2-chloroethyloxycarbonyl, 2,2,2-trichloroethyloxycarbonyl, 3-methyl-1,4-dihydropyridin-1-ylcarbonylaminomethyloxycarbonyl, etc); ($C_{3-8}$)cycloalkyloxycarbonyls such as cyclopentyloxycarbonyl and cyclohexyloxycarbonyl (These may be substituted by halogen such as chlorine, bromine, iodine, etc.); cycloalkylalkyloxycarbonyls such as cyclopentylmethyloxycarbonyl; ($C_{2-7}$)alkenyl- or alkynyloxycarbonyls such as allyloxycarbonyl, crotyloxycarbonyl and 2-pentene-1-oxycarbonyl; and aromatic or aromatoaliphatic oxycarbonyls such as phenyloxycarbonyl, benzyloxycarbonyl and phenethyloxycarbonyl. (The aromatic or aromatoaliphatic oxycarbonyl may be substituted by halogen such as chlorine, bromine, iodine, etc.), quinuclidinyloxycarbonyl.

In the compound represented by the above formula (I), hydrogen; ($C_{1-6}$)alkyl groups such as methyl, ethyl and propyl; and ($C_{1-4}$) alkyloxycarbonyls such as methyloxycarbonyl and ethyloxycarbonyl; ($C_{6-8}$) araomatoaliphatic oxycarbonyl such as benzyloxycarbonyl, specifically hydrogen, ($C_{1-4}$) alkyl groups and halogenated ($C_{1-4}$)alkyl groups are preferable for $R_1$. It is preferable that Y be oxygen; in such cases, hydrocarbon residues which may have a substituent, specifically ($C_{1-6}$)alkyls such as methyl, ethyl, propyl, isopropyl and butyl, and alkyl halides such as chloromethyl, are preferable for $R_2$. It is preferable that each of $X_1$ and $X_2$ is oxygen. It is preferable that $R_3$ be hydrogen. It is preferable that m is 0 and that n is 0. It is preferable that $R_1$ is hydrogen or a hydrocarbon residue which may be substituted when m is 1.

When the compound (I) of the present invention is basic, it may form acid-adducts of salt, specifically physiologically acceptable acid-adducts of salt. As examples of such acid-adducts of salt, mention may be made of salts of inorganic acids (e.g., hydrochloric acid, nitric acid, phosphoric acid and hydrobromic acid) or organic acids (e.g., acetic acid, propionic acid, fumaric acid, maleic acid, tartaric acid, citric acid, malic acid, oxalic acid, benzoic acid, methanesulfonic acid and benzenesulfonic acid).

The compound (I) wherein m is 0 can be produced by cyclizing for example a compound of the formula:

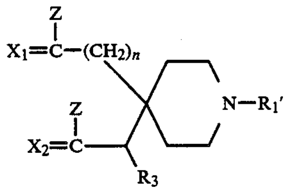

(II)

wherein $X_1$, $X_2$, n and $R_3$ are of the same meanings as above; $R_1'$ is of the same meaning as of the above $R_1$ or is $R_1$, whose functional group has been protected by a protective group when $R_1$ has a functional group such as hydroxyl, carboxyl, amino, etc.; Z represents a leaving group, with for example a compound of the formula:

$$NH_2—Y—R_2' \quad (III)$$

wherein Y is of the same meaning as above, and $R_2'$ is of the same meaning as of the above $R_2$ or is an $R_2$ whose functional group has been protected by a protective group when $R_2$ has a functional group such as hydroxyl, carboxyl, amino, etc., if necessary eliminating $R_1'$ or $R_2'$ itself or the protective groups contained in $R_1'$ and $R_2'$.

In the compound (II), as examples of leaving groups represented by Z, mention may be made of hydroxy, ($C_{1-4}$)alkyloxys (e.g., methyloxy, ethyloxy, propyloxy and butyloxy), halogens (e.g., fluorine, chlorine, bromine, and iodine), N-hydroxydiacylimide esters (e.g., N-hydroxysuccinimide ester, N-hydroxyphthalimide esters and N-hydroxy-5-norbornene-2,3-dicarboxyimide ester), N-hydroxybenzotriazole ester, para-nitrophenyl ester and phenyl ester.

In the compounds of the formulas (II) and (III), any protective group can be used in the functional groups contained in $R_1'$ and $R_2'$, as long as it is a well-known, normally used protective group, for example the tertiary butyloxycarbonyl and benzyloxycarbonyl groups as protective groups for amino group; benzyl, methyl, ethyl and tertiary butyl ester as protective groups for carboxyl; and benzyl, p-methoxybenzyl, trityl and acetyl groups as protective groups for the hydroxyl group.

In this condensation cyclization reaction, it is not always necessary to use a solvent, but when a solvent is used, it is normally recommended that the solvent be chosen from among organic solvents such as hydrocarbon solvents (e.g., pentane, hexane, benzene and toluene), halogenated hydrocarbon solvents (e.g., dichloromethane, chloroform, dichloroethane and carbon tetrachloride), ether solvents (e.g., ethyl ether, tetrahydrofuran, dioxane and dimethoxyethane), amide solvents (e.g., dimethylformamide and hexamethylphosphonotriamide) and dimethylsulfoxide. It is preferable to use 1 to 3 moles of compound (III) per mole of compound (II). The reaction can be carried out between −10° C. and 200° C.

The compound (I) can also be produced by reacting the product obtained by derivatizing, by a well-known method, the compound of the formula (II), wherein Z is hydroxy, into an acid anhydride, with a compound of the formula (III) and then cyclizing this compound by a well known method.

In the above description, as examples of well-known methods of derivatizing into an acid anhydride the compound (II), wherein Z is hydroxy, mention may be made of the direct heating method and methods using as dehydrating agents, phosphoryl chloride, acid anhydrides of lower fatty acid (e.g., acetic anhydride and trifluoroacetic anhydride), haloformates (e.g., ethyl chloroformate), imidazole derivatives (e.g., N,N'-carbodiimidazole, N-trifluoroacetylimidazole and N-trichloroacetylimidazole) and dicyclohexylcarbodiimide.

As examples of well-known methods of cyclizing the product obtained by reacting an acid anhydride of the compound (II), wherein Z is hydroxy, with the compound represented by the formula (III), mention may be made of methods in which the subject product is heated directly or in a solvent, if necessary, in the presence of an acid catalyst (e.g., hydrogen chloride, hydrogen bromide, methanesulfonic acid, benzenesulfonic acid and toluenesulfonic acid). As solvents for these reactions, any solvent can be used, as long as it is a generally used solvent; the use of an inert solvent is preferable, such as chloroform, dichloroethane, benzene, toluene, acetonitrile, dioxane, tetrahydrofuran, dimethylformamide or dimethylsulfoxide. Acid anhydrides of lower fatty acid (e.g., acetic anhydride and trifluoroacetic anhydride) can also be used; in cases where these are used, the reaction is carried out in the presence of an alkali metal salt of lower fatty acid (e.g., sodium acetate, potassium acetate or sodium trifluoroacetate). The reaction is carried out mainly between 40° C. and 200° C., but heating is not always necessary.

The compound (I) wherein m is 0 can be produced by reacting, for example, a compound of the formula:

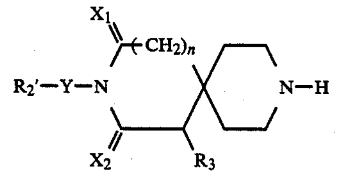

(Ia)

wherein $R_2'$, $R_3$, $X_1$, $X_2$, Y, and n are of the same meaning as above, with, for example, a compound of the formula:

$$R_1'—Z \qquad (IV)$$

wherein $R_1'$ and Z are of the same meanings are above, and, if necessary, eliminating the protective groups.

Any solvents can be used for the reaction, as long as they are generally used for chemical reactions. The reactions can be carried out, for example, in an inert solvent such as water, chloroform, dichloroethane, benzene, toluene, acetonitrile, dioxane, tetrahydrofuran or dimethylformamide, for example between −10° C. and 120° C. It is preferable to use 1 to 3 moles of compound (IV) per mole of compound (Ia). In addition, this reaction may be carried out, if necessary, in the presence of organic bases such as pyridine, 4-dimethyl aminopyridine, triethylamine, diisopropylamine, triethyleneamine or tetramethylethylenediamine; inorganic bases such as sodium hydrogencarbonate, potassium hydrogencarbonate, sodium carbonate, potassium carbonate, sodium hydroxide or potassium hydroxide; sodium hydride; potassium hydride; or n-bytyllithium. It is preferable to use 1 to 3 moles of the base per mole of compound (Ia).

The compound (I) wherein m is 0 can also be produced by reacting the compound (Ia) with a compound of the formula:

$$R_1'—N{=}C{=}O \qquad (V)$$

wherein $R_1'$ is of the same meaning as above, and if necessary, eliminating the protective groups.

This reaction can usually be carried out in the presence of a suitable solvent. As examples of the solvent, mention is made of halogenated aliphatic hydrocarbons (e.g. dichloromethane, chloroform), aromatic hydrocarbon (e.g. benzene, toluene, xylene), ethers (e.g. diethylether, dioxane, tetrahydrofuran), dimethylformamide. The reaction temperature is usually from room temperature to 60° C. It is preferable to use 1 to 3 mole of compound (V) per mole of compound (Ia). The reaction is preferably carried out in the presence of an organic base such as trimethylamine, triethylamine, dimethylaminopyridine. The amount of the base used is preferably 1 to 3 moles per mole of compound (Ia).

The compound (I) wherein m is 0 can also be produced by reacting for example a compound of formula:

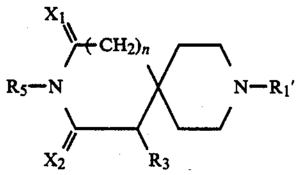

(Ib)

wherein $R_1'$, $R_3$, $X_1$, $X_2$ and n are of the same meanings as above, and $R_5$ represents hydrogen or hydroxy with for example a compound of the formula:

$$R_2'—Z' \qquad (VI)$$

wherein $R_2'$ is of the same meaning as above, and Z' represents halogen (e.g. chlorine, bromine or iodine), and if necessary, eliminating the protective groups. As solvents for these reactions, solvents such as alcohols (e.g. methanol, ethanol), halogenated hydrocarbons (e.g. dichloromethane, chloroform), ethers (e.g. tetrahydrofuran, dioxane), dimethylformamide or acetonitrile can be used. This reaction is carried out, if necessary, in the presence of, for example, sodium hydrogencarbonate, potassium hydrogencarbonate, sodium carbonate, potassium carbonate, sodium hydroxide, potassium hydroxide, sodium methoxide, sodium ethoxide, sodium hydride, potassium hydride or n-butyllithium, reaction temperature being normally between −10° C. and 150° C. It is preferable to use 1 to 3 moles of compound (VI) per mole of compound (Ib).

The compound (I) wherein m is 0 can also be produced by reacting, for example, a compound of the formula:

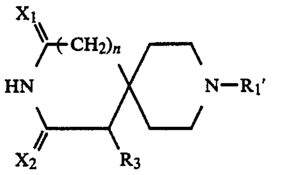
(Ic)

wherein $R_1'$, $R_3$ and n have the same definitions as above, with, for example, a compound of the formula:

$R_2'$—S—Z' (VII)

wherein $R_2'$ and Z' have the same definitions as above, and, if necessary, eliminating the protective groups. This reaction is carried out in a similar manner to the reaction between the compound (Ib) and compound (VI).

The production of the compound (Id):

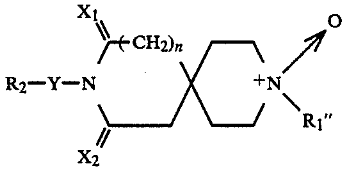
(Id)

wherein $R_2$, $X_1$, $X_2$, Y and n have the same definitions as above, and $R_1''$ represents a lower alkyl having 1 to 4 carbon atoms which may be substituted among others represented by $R_1$ as defined above, can be carried out by the method in which for example a compound of the formula:

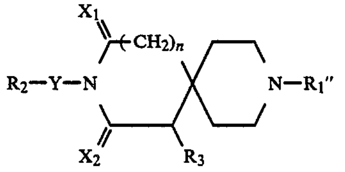
(Ie)

wherein $R_1''$, $R_2$, $R_3$, $X_1$, $X_2$, Y and n have the same definitions as above, is subjected to reaction using a known oxidizing agent to produce an N-oxide. As examples of oxidizing agents referred to herein, mention may be made of hydrogen peroxide, and organic peroxy acids (e.g., peracetic acid and metachloroperbenzoic acid). It is preferable to use 1 to 3 moles of the oxidizing agent per mole of compound (Ie). The reaction temperature is in the range of from −10° C. to 60° C.

The starting material, the compound of the formula (II), wherein Z is hydroxy or a lower ($C_{1-4}$)alkoxy, is produced in accordance with the method described in Helv. Chim Acta., 49, 1135 (1966), Arch. Pharm., 294, 210 (1961), J. Am. Chem. Soc., 71, 384 (1950) or Belgian Pat. No. 609766, or by hydrolyzing the product with an acid or alkali. Hydrolysis can easily be achieved by a well-known method, e.g., hydrolysis, using, for example, an alkali metal hydroxide (e.g., sodium hydroxide, lithium hydroxide or potassium hydroxide), an alkali metal carbonate (e.g., potassium carbonate, sodium carbonate or lithium carbonate) or a mineral acid (e.g., hydrochloric acid, sulfuric acid, nitric acid, phosphoric acid or iodic acid). The starting compound can also be produced by converting $R_1'$ of the compound of the general formula (II) into hydrogen by a well-known method, and subsequently reacting, by a well-known method, the compound (VIII) thus obtained:

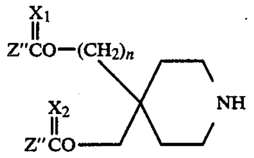
(VIII)

wherein $X^1$, $X_2$ and n have the same definitions as above, and Z'' represents hydroxy or ($C_{1-4}$)alkoxy, with the compound (IV) or the compound (V). Well-known methods of producing the compound (VIII) are efficient catalytic hydrogen reduction, in cases where $R_1'$ in the general formula (II) is a benzyl group, and acid hydrolysis in cases where $R_1'$ is an acyl group. For the reaction between the compound (VIII) and compounds (VI) or (V), any generally used solvent can be used. For example, this reaction is carried out in an inert solvent such as water, chloroform, dichloroethane, benzene, toluene, acetonitrile, dioxane, tetrahydrofuran or dimethylformamide, and, if necessary, in the presence of organic bases such as pyridine, 4-dimethylaminopyridine, triethylamine, diisopropylamine, triethylenediamine and tetramethylethylenediamine; inorganic bases such as sodium hydrogencarbonate, potassium hydrogencarbonate, sodium carbonate, potassim carbonate, sodium hydroxide and potassium hydroxide; sodium hydride; potassium hydride or n-butyllithium.

As to the compound (II), the compound having halogen for Z, which is an acid halide, can be produced by halogenating the compound having for Z hydroxy, which is a carboxylic acid, by a well-known method, for example, using a halogenating agent (e.g., phosphorus oxychloride, phosphorus oxybromide, phosphorus pentachloride, phosphorus pentabromide, phosphorus trichloride, phosphorus tribromide, thionyl chloride, thionyl bromide, sulfuryl chioride, oxalyl chloride, cyanuric chloride, boron tribromide or hydrogen iodide).

Any normally used solvent can be used for this halogenation; inert solvents such as chloroform, dichloromethane, dichloroethane, benzene or toluene are preferable.

As to the compound (II), the compound having for Z N-hydroxydiacylimide ester, N-hydroxybenzotriazole ester, para-nitrophenol ester or phenol ester can be produced by a well-known method, for example, by condensing the compound having for Z hydroxy, which is a carboxylic acid, using dicyclohexylcarbodiimide as a condensing agent, in the presence of N-hydroxydiacylimide, N-hydroxybenzotriazole, para-nitrophenol or phenol.

Any normally used solvent can be used for the above reaction; inert solvents such as chloroform, dichloromethane, dichloroethane, benzene, toluene, N,N-dimethylformamide, tetrahydrofuran or dioxane are preferable.

The compound (I) of the present invention was found to act on the central nervous system of mammals, possess strong specific affinity to the muscarinic acetylcholine receptor, and exhibit antiamnesiac action on various amnesia-inducing actions in mice.

Compared with the above mentioned known azaspiro derivatives and those drugs now commercially available as acetylcholine antagonists, the compound (I) of the present invention shows far more selectivity between action on the central and peripheral nervous systems at a dose at which antiamnesiac action appears in mice (0.03 to 10 mg/body), the compound has no effect on the peripheral nerves, such as in convulsions, salivation or diarrhea, or, if any, the effect is very weak; in addition, it exhibits a noticeable effect via oral administration. The compound (I) of the present invention is thus useful as a brain function-improving drug in mammals, including humans.

As examples of diseases on which the compound of the present invention is effective, mention may be made of senile dementia, Alzheimer's disease, Huntington's chorea, hyperkinesia and mania; the compound of the present invention can be used to prevent or treat these diseases.

The compound of the present invention can be administered orally or parenterally to mammals, including humans, in various dosage forms such as tablets, granules, capsules, injections and suppositories. The administration amount, which varies with types of subject diseases, symptoms, etc., is normally 0.1 mg to 500 mg, preferably 1 mg to 50 mg, most preferably 1 mg to 10 mg per day for adults in the case of oral administration.

The present invention is hereinafter described in more detail with some examples of the subject compounds, examples of pharmaceutical preparations and an experiment.

EXAMPLE 1

2-Methoxy-8-methyl-2,8-diazaspiro[4,5]decane-1,3-dione hydrochloride

After stirring at 100° C. for 24 hours a solution of (1-methyl-4-carboethoxypiperidin-4-yl) acetic acid ethyl ester (60 g) in concentrated hydrochloric acid (400 ml), the solvent was evaporated off under reduced pressure, and the residue was dried. The resulting (1-methyl-4-carboxypiperidin-4-yl) acetic acid hydrochloride (0.47 g) was dissolved in dimethylformamide (10 ml). To the resulting solution dicyclohexylcarbodiimide (0.45 g) was added, and this was followed by stirring at room temperature for 1 hour. o-Methylhydroxylamine hydrochloride (0.17 g) and triethylamine (0.28 ml) were then added, and this was followed by stirring at room temperature for 30 minutes. The resulting precipitates were removed, and the solvent was evaporated off under reduced pressure. To the residual oily compound acetic anhydride (8 ml) and anhydrous sodium acetate (420 mg) were added, and this was followed by stirring at 100° C. for 30 minutes. After the reaction, the solvent was evaporated off under reduced pressure, and acetonitrile (30 ml) was added to the residue to remove the insoluble substances, then the acetonitrile was evaporated off under reduced pressure. To the resulting residue 1N hydrochloric acid (3 ml) and water (20 ml) were added to remove the insoluble substances. The residual solid was recrystallized from ethanol-ethyl acetate ester to obtain 0.35 g of a colorless crystal having a melting point of 259° C.

Elemental analysis (as $C_{10}H_{17}ClN_2O_3$): Calculated: C, 48.29; H, 6.89; N, 11.26 Found: C, 48.18; H, 6.90; N, 10.97.

EXAMPLE 2

3-Methoxy-9-methyl-3,9-diazaspiro[5,5]undecane-2,4-dione hydrochloride

After stirring at 100° C. for 24 hours of a solution of 1-methyl-4,4-dicarboxymethylpiperidine ethyl ester (30 g) in concentrated hydrochloric acid (200 ml), the solvent was evaporated off under reduced pressure, and the residue was dried. The resulting 1-methyl-4,4-dicarboxymethylpiperidine hydrochloride (0.50 g) was subjected to the same procedure as in Example 1 to obtain 0.23 g of a colorless crystal having a melting point of from 275° to 284° C.

Elemental analysis (as $C_{11}H_{19}ClN_2O_3$): Calculated: C, 50.29; H, 7.29; N, 10.66 Found: C, 50.35; H, 7.17; N, 10.57.

EXAMPLE 3

8-Benzyl-2-methoxy-2,8-diazaspiro[4,5]decane-1,3-dione hydrochloride

After stirring at 100° C. for 24 hours of a solution of (1-benzyl-4-carboethoxy-piperidin-4-yl)acetic acid ethyl ester (60 g) in concentrated hydrochloric acid (400 ml), the solvent was evaporated off under reduced pressure, and this was followed by drying. The resulting (1-benzyl-4-carboxy-piperidin-4-yl)acetic acid hydrochloride (0.94 g) was subjected to the same procedure as in Example 1 to obtain 0.28 g of a colorless crystal having a melting point of from 227° to 229° C.

Elemental analysis (as $C_{16}H_{21}ClN_2O_3$): Calculated: C, 59.17; H, 6.52; N, 8.62 Found: C, 59.21; H, 6.62; N, 8.50.

EXAMPLE 4

The compounds listed in Table 1 were obtained in the same manner as in Examples 1, 2 and 3.

TABLE 1

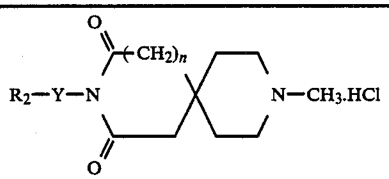

| Compound Number | Method of Reaction | $R_2$ | Y | n | Melting Point (°C.) | Molecular Formula | Elemental Analysis Calculated Found C | H | N |
|---|---|---|---|---|---|---|---|---|---|
| 1 | 1 | 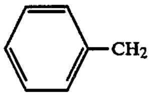 | O | 0 | 261-263 | $C_{16}H_{21}ClN_2O_3$ | 46.06 (46.13) | 6.44 (6.65) | 11.94 (12.11) |
| 2 | 1 | $CH_3$ | 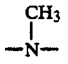 | 0 | 229-230 | $C_{11}H_{20}ClN_3O_2$ | 50.47 (50.30) | 7.70 (7.81) | 16.05 (16.01) |
| 3 | 2 | $CH_3$ | 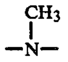 | 1 | 169-175 | $C_{12}H_{22}ClN_3O_2$ | 52.26 (52.13) | 8.04 (8.19) | 15.24 (15.07) |
| 4 | 3 | 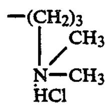 | O | 0 | 231-234 | $C_{14}H_{27}Cl_2N_3O_3$ | 46.49 (46.60) | 7.69 (7.76) | 11.62 (11.36) |

Note:
Method of Reaction 1 is as of Example 1, and Method of Reaction 2, Example 2.

EXAMPLE 5

2-Hydroxy-8-methyl-2,8-diazaspiro[4,5]decane-1,3-dione hydrochloride

The compound No. 1 (2-benzyloxy-8-methyl-2,8-diazaspiro[4,5]decane-1,3-dione hydrochloride (6.4 g), listed in Table 1 in Example 4) was dissolved in 50 ml of methanol-water (1 to 1, v/v), and this was followed by catalytic hydrogen reduction for about 1 hour in the presence of palladium catalyst. The resulting solid was recrystallized from ethanol to obtain 4.3 g of a colorless crystal having a melting point of from 284° to 286° C.

Elemental analysis (as $C_9H_{15}ClN_2O_3$): Calculated: C, 46.06; H, 6.44; N, 11.94 Found: C, 46.13; H, 6.65; N, 12.11.

EXAMPLE 6

2-Ethyloxy-8-methyl-2,8-diazaspiro[4,5]decane-1,3-dione hydrochloride

2-Hydroxy-8-methyl-2,8-diazaspiro[4,5]decane-1,3-dione hydrochloride (1.05 g) which was obtained in Example 5 was suspended in dimethylformamide (45 ml). To the resulting suspension sodium hydride (60% in oil) (0.36 g) was added, and this was followed by stirring at room temperature for 1 hour. Ethyl iodide (0.36 ml) was then added, and this was followed by stirring at room temperature for 2 hours. The solvent was evaporated off under reduced pressure, and the insoluble substances were removed after adding ethanol (20 ml) and 3.2N hydrogen chloride in dioxane (2 ml). The solvent was evaporated off under reduced pressure to give residual solid, which was recrystallized from ethanol-ethyl acetate to obtain 0.6 g of a colorless crystal having a melting point of from 222° to 225° C.

Elemental analysis (as $C_{11}H_{19}ClN_2O_3$): Calculated: C, 50.29; H, 7.29; N, 10.66 Found: C, 50.25; H, 7.25; N, 10.76.

EXAMPLE 7

The compounds listed in Table 2 were obtained in the same manner as in Example 6.

TABLE 2

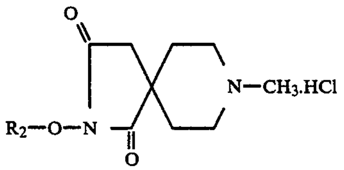

| Compound Number | $R_2$ | Melting Point (°C.) | Molecular Formula | Elemental Analysis Calculated (Found) C | H | N |
|---|---|---|---|---|---|---|
| 1 | $(CH_2)_2CH_3$ | 231-234 | $C_{12}H_{12}ClN_2O_3$ | 52.08 (51.84) | 7.65 (7.89) | 10.12 (10.10) |
| 2 | $CH(CH_3)_2$ | 259-271 | $C_{12}H_{21}ClN_2O_3$ | 52.08 (51.97) | 7.65 (7.86) | 10.12 (10.09) |

TABLE 2-continued

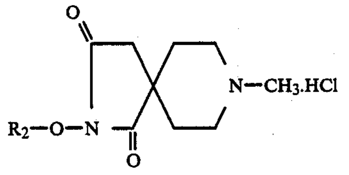

| Compound Number | $R_2$ | Melting Point (°C.) | Molecular Formula | Elemental Analysis Calculated (Found) C | H | N |
|---|---|---|---|---|---|---|
| 3 | $(CH_2)_3CH_3$ | 179 | $C_{13}H_{23}ClN_2O_3$ | 53.70 (53.66) | 7.97 (7.98) | 9.63 (9.50) |
| 4 | $CH_2Cl$ | 195–198 | $C_{11}H_{16}Cl_2N_2O_3$ | 41.11 (41.34) | 5.86 (6.03) | 9.59 (9.69) |
| 5 | $CH_2OCH_3$ | 205–207 | $C_{11}H_{19}ClN_2O_4$ | 47.40 (47.26) | 6.87 (6.87) | 10.05 (9.74) |
| 6 | $CH_2SCH_3$ | 83–85 | $C_{11}H_{19}ClN_2O_3S_1$ | 44.82 (44.81) | 6.50 (6.35) | 9.50 (9.40) |

EXAMPLE 8

8-Benzyloxycarbonyl-2-methoxy-2,8-diazaspiro[4,5]-decane-1,3-dione (1) (1-Benzyl-4-carboxypiperidin-4-yl)acetic acid hydrochloride (4.56 g) was dissolved in water (20 ml), and subjected to catalytic hydrogen reduction using palladium as a catalyst at 80° C. under normal pressure for 8 hours. After the reaction, the catalyst was removed. To this solution sodium hydrogencarbonate (3.6 g) and benzyloxycarbonyl chloride (3 ml) were added, and this was followed by stirring at room temperature for one night. After the reaction mixture was extracted with ethylether (48 ml), the aqueous layer was adjusted to pH 3 with 1N hydrochloric acid, and the resulting oily substance was extracted with chloroform. After drying the chloroform solution with anhydrous magnesium sulfate, the solvent was evaporated off. The resulting residual solid was recrystallized from ethyl ether to obtain 3.8 g (1-benzyloxycarbonyl-4-carboxypiperidin-4-yl)acetic acid in the form of a colorless crystal having a melting point of from 125° to 127° C.

Elemental analysis (as $C_{16}H_{19}NO_6$): Calculated: C, 59.81; H, 5.96; N, 4.36 Found: C, 59.61; H, 5.95; N, 4.56.

(2) To a solution of (1-benzyloxycarbonyl-4-carboxypiperidin-4-yl)acetic acid (3.64 g) in dimethylformamide (30 ml) dicyclohexylcarbodiimide (2.57 g) was added, and this was followed by stirring at room temperature for 30 minutes. o-Methylhydroxylamine hydrochloride (0.95 g) and triethylamine (1.56 ml) were then added, and this was followed by stirring at room temperature for 30 minutes. The resulting precipitates were removed, and the solvent was evaporated under reduced pressure. To the resulting residual oily compound acetic anhydride (20 ml) and anhydrous sodium acetate (0.39 g) were added, and this was followed by stirring at 100° C. for 30 minutes. After the completion of the reaction, the solvent was removed, and the residual oil was dissolved in 50 ml ethyl acetate. The resulting solution was sequentially washed with a saturated aqueous solution of sodium hydrogencarbonate, 1N hydrochloric acid and water, and dried with anhydrous magnesium sulfate. The solvent was evaporated under reduced pressure; the resulting residual solid was recrystallized from ethyl ether-petroleum ether to obtain 2.1 g of a colorless crystal having a melting point of 98° C.

Elemental analysis (as $C_{17}H_{20}N_2O_5$): Calculated: C, 61.44; H, 6.07; N, 8.43 Found: C, 61.39; H, 6.10; N, 8.58.

EXAMPLE 9

2-Methoxy-2,8-diazaspiro[4,5]decane-1,3-dionehydrochloride

8-Benzyloxycarbonyl-2-methoxy-2,8-diazaspiro[4,5]-decane-1,3-dione (2.0 g) which was obtained in Example 8 was dissolved in a mixture of methanol (30 ml) and of 1N hydrochloric acid (10 ml), and subjected to catalytic reduction using palladium as a catalyst at normal temperature under atmospheric pressure for 5 hours. After the reaction, the catalyst was removed, and the solvent was evaporated off. The resulting residual solid was recrystallized from ethanol-ethyl acetate to obtain 1.2 g of a colorless crystal having a melting point of from 265° to 273° C.

Elemental analysis (as $C_9H_{15}ClN_2O_3$): Calculated: C, 46.06; H, 6.44; N, 11.94 Found: C, 45.91; H, 6.46; N, 12.03.

This compound could also be synthesized by the following method:

8-Benzyl-2-methoxy-2,8-diazaspiro[4,5]decane-1,3-dione hydrochloride (3.24 g) which was obtained in Example 3 was dissolved in water (20 ml), and subjected to catalytic reduction using palladium as a catalyst at 80° C. under atmospheric pressure for 5 hours. This solution was then treated in the same manner as above to obtain 2.1 g of the desired product in the form of a colorless crystal having a melting point of from 265° to 273° C.

Elemental analysis (as $C_9H_{15}ClN_2O_3$): Calculated: C, 46.06; H, 6.44; N, 11.94 Found: C, 46.12; H, 6.51; N, 11.78.

EXAMPLE 10

8-[3-(Ethyloxycarbonyl)propyl]-2-methoxy-2,8-diazaspiro[4,5]decane-1,3-dione hydrochloride 2-Methoxy-2,8-diazaspiro[4,5]decane-1,3-dione hydrochloride (1.76 g) which was obtained in Example 9 was suspended in dimethylformamide (50 ml). To the resulting suspension sodium hydride (60% in oil) (0.66 g) was added, and this was followed by stirring at room temperature for 1 hour. 3-Bromopropionic acid ethyl ester (1.07 ml) was then added, and this was followed by stirring at room temperature for one day. After the reaction, the resulting precipitates were removed, and the solvent was evaporated under reduced pressure, and this was directly followed by silica gel column chromatography (eluent: chloroform:methanol:water=14:6:1 (v/v)). After adding a solution of 3.2N hydrogen chloride in dioxane (3 ml) to the solution containing the desired product, the solvent was evaporated off. The resulting residual solid was recrystallized from ethanol-ethyl acetate to obtain 1.33 g of a white crystal having a melting point of from 174° to 176° C.

Elemental analysis (as $C_{15}H_{25}ClN_2O_5$): Calculated: C, 51.65; H, 7.22; N, 8.03 Found: C, 51.14; H, 7.28; N, 8.19.

EXAMPLE 11

The compounds listed in Table 3 were obtained in the same manner as in Example 10.

TABLE 3

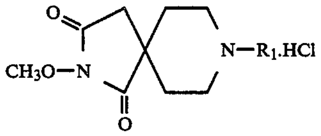

| Compound Number | $R_1$ | Melting Point (°C.) | Molecular Formula | Elemental Analysis Calculated (Found) C | H | N |
|---|---|---|---|---|---|---|
| 1 | $CH_2CH_3$ | 232–235 | $C_{11}H_{19}ClN_2O_3$ | 50.29 (50.21) | 7.29 (7.32) | 10.66 (10.71) |
| 2 | $(CH_2)_2CH_3$ | 192 | $C_{12}H_{21}ClN_2O_3$ | 52.08 (52.01) | 7.65 (7.53) | 10.12 (10.18) |
| 3 | $CH_2CONH_2$ | 234–242 | $C_{11}H_{18}ClN_3O_4$ | 45.29 (45.28) | 6.22 (6.51) | 14.40 (14.45) |

EXAMPLE 12

2-Methoxy-8-methylcarbamoyl-2,8-diazaspiro[4,5]decane-1,3-dione

To a solution of 2-methoxy-2,8-diazaspiro[4,5]decane-1,3-dione hydrochloride (1.5 g) in water (20 ml) was added triethylamine (1 ml), followed by methyl isocyanate (1 ml), and this was followed by stirring at room temperature for 30 minutes. The water was then evaporated off under reduced pressure. The residue was directly subjected to silica gel column chromatography (eluent; chloroform-acetone-methanol=10:3:2 (v/v)), and the solvent for the solution containing the desired product was evaporated off under reduced pressure to obtain 1.4 g of a colorless oily compound.

Elemental analysis (as $C_{11}H_{17}N_3O_4$): Calculated: C, 51.76; H, 6.71; N, 16.46 Found: C, 51.64; H, 6.83; N, 16.47.

EXAMPLE 13

8-tert-Butyloxycarbonyl-2-methoxy-2,8-diazaspiro[4,5]-decane-1,3-dione

To a solution of 2-methoxy-2,8-diazaspiro[4,5]decane-1,3-dione hydrochloride (1.5 g) in dimethylformamide (100 ml) was added triethylamine (1 ml), followed by tert-butyl dicarbonate (2.05 ml), and this was followed by stirring at room temperature for 1 hour. The solvent was evaporated off under reduced pressure. To the residual oil dichloromethane (50 ml) was added, after which it was washed with a 10% aqueous solution of citric acid, then with water. After drying the organic layer with anhydrous magnesium sulfate, the solvent was evaporated under reduced pressure. The resulting residual solid was recrystallized with ethyl ether to obtain 1.4 g of a colorless crystal having a melting point of 117° C.

Elemental analysis (as $C_{14}H_{22}N_2O_5$): Calculated: C, 56.36; H, 7.43; N, 9.39 Found: C, 56.57; H, 7.39; N, 9.55.

EXAMPLE 14

8-Acetyl-2-methoxy-2,8-diazaspiro[4,5]decane-1,3-dione

To a solution of 2-methoxy-2,8-diazaspiro[4,5]decane-1,3-dione hydrochloride (2.35 g) in dimethylformamide (200 ml) was added triethylamine (2.8 ml), followed by acetyl chloride (0.8 ml), and this was followed by 30 minutes of stirring at room temperature. To the resulting residual oily substance dichloromethane (50 ml) was added, after which it was washed with 1N hydrochloric acid and then with water. After drying the organic layer with anhydrous magnesium sulfate, the solvent was evaporated under reduced pressure; the resulting residual solid was recrystallized from ethanol-ethyl ether to obtain 1.2 g of a colorless crystal having a melting point of from 153° to 157° C.

Elemental analysis (as $C_{11}H_{16}N_2O_4$): Calculated: C, 54.99; H, 6.71; N, 11.66 Found: C, 54.72; H, 6.98; N, 11.31.

EXAMPLE 15

The compounds shown in Table 4 were obtained in the same manner as in Example 14.

TABLE 4

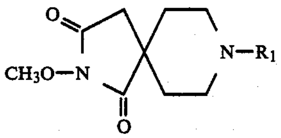

| Compound Number | $R_1$ | Melting Point (°C.) | Molecular Formula | Elemental Analysis Calculated (Found) C | H | N |
|---|---|---|---|---|---|---|
| 1 | 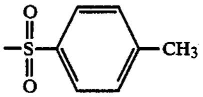 | 212–214 | $C_{16}H_{20}N_2O_5S$ | 54.53 (54.69) | 5.72 (5.90) | 7.95 (8.08) |
| 2 | 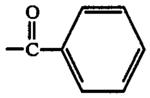 | 140–143 | $C_{16}H_{18}N_2O_3$ | 62.63 (62.79) | 6.08 (5.84) | 9.13 (9.30) |
| 3 | 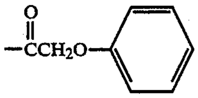 | 118–119 | $C_{17}H_{20}N_2O_5$ | 61.44 (61.26) | 6.07 (6.11) | 8.43 (8.50) |
| 4 | $-\overset{\overset{O}{\parallel}}{C}OCH_3$ | 128 | $C_{11}H_{16}N_2O_5$ | 51.56 (51.56) | 6.29 (6.37) | 10.93 (10.74) |
| 5 | $-\overset{\overset{O}{\parallel}}{C}OCH_2CH_2Br$ | 134 | $C_{12}H_{17}BrN_2O_5$ | 41.28 (41.33) | 4.91 (4.96) | 8.02 (8.03) |
| 6 | $-\overset{\overset{O}{\parallel}}{C}OCH_2CH_3$ | 88–90 | $C_{12}H_{18}N_2O_5$ | 53.33 (53.05) | 6.71 (6.71) | 10.36 (10.30) |
| 7 | $-\overset{\overset{O}{\parallel}}{C}OCH_2CH_2CH_3$ | 93–95 | $C_{13}H_{20}N_2O_5$ | 54.92 (55.07) | 7.09 (7.03) | 9.85 (9.86) |
| 8 | $-\overset{\overset{O}{\parallel}}{C}O(CH_2)_3CH_3$ | 83–84 | $C_{14}H_{22}N_2O_5$ | 56.36 (56.60) | 7.43 (7.50) | 9.39 (9.31) |
| 9 | $-\overset{\overset{O}{\parallel}}{C}O(CH_2)_5CH_3$ | 48–49 | $C_{16}H_{26}N_2O_5$ | 58.88 (58.93) | 8.03 (8.23) | 8.58 (8.44) |
| 10 | $-\overset{\overset{O}{\parallel}}{C}OCH(CH_3)_2$ | 123 | $C_{13}H_{20}N_2O_5$ | 54.92 (54.70) | 7.07 (7.08) | 9.85 (9.92) |
| 11 | $-\overset{\overset{O}{\parallel}}{C}OCH_2CH{=}CH_2$ | 71–72 | $C_{13}H_{18}N_2O_5$ | 55.31 (55.33) | 6.43 (6.52) | 9.92 (9.66) |
| 12 | $-\overset{\overset{O}{\parallel}}{C}OCH_2CCl_3$ | 132–133 | $C_{12}H_{15}Cl_3N_2O_5$ | 38.58 (38.68) | 4.05 (3.95) | 7.50 (7.55) |
| 13 | 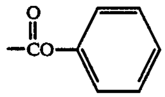 | 175–177 | $C_{16}H_{18}N_2O_5$ | 60.37 (60.09) | 5.70 (5.77) | 8.80 (9.00) |
| 14 | 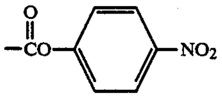 | 193–194 | $C_{16}H_{17}N_3O_7$ | 52.89 (52.75) | 4.72 (4.72) | 11.57 (11.52) |

EXAMPLE 16

8-Aminoacetyl-2-methoxy-2,8-diazaspiro[4,5]decane-1,3-dione hydrochloride (1) To a solution of 2-methoxy-2,8-diazaspiro[4,5]-decane-1,3-dione hydrochloride (1.5 g) in dimethylformamide (100 ml) were added triethylamine (1 ml), tert-butyloxycarbonylglycine (1.23 g), and then dicyclohexylcarbodiimide (1.44 g), and this was followed by stirring at 60° C. for 10 hours. After the reaction, the solvent was evaporated under reduced pressure. The resulting residual oily substance was dissolved in dichloromethane (50 ml), after which it was washed with a 10% aqueous solution of citric acid and then with water. The organic layer was then dried with anhydrous magnesium sulfate, and this was followed by the evaporation of the solvent under reduced pressure. The resulting residual solid was recrystallized from ethyl acetate-ethyl ether to obtain 1.1 g of a colorless crystal (8-tert-butyloxycarbonylaminoacetyl-2-methoxy-2,8-diazaspiro[4,5]decane-1,3-dione) having a melting point of 151° C.

Elemental analysis (as $C_{16}H_{25}O_6N_3$): Calculated: C, 54.07; H, 7.09; N, 11.82 Found: C, 54.19; H, 7.21; N, 11.79.

(2) To 8-tert-butyloxycarbonylaminoacetyl-2-methoxy-2,8-diazaspiro[4,5]decane-1,3-dione (1.0 g) which was obtained above, a solution of 6N hydrogen chloride in ethanol (5 ml) was added, and it was kept standing at room temperature for 10 minutes. The solvent was then evaporated under reduced pressure, and this was followed by recrystallization from ethyl acetate-ethyl ether to obtain 0.8 g of a colorless crystal having a melting point of from 97° to 102° C.

Elemental analysis (as $C_{11}H_{18}ClN_3O_4$): Calculated: C, 45.28; H, 6.22; N, 14.40 Found: C, 45.25; H, 6.24; N, 14.36.

EXAMPLE 17

8-(4-Aminobutyryl)-2-methoxy-2,8-diazaspiro[4,5]decane-1,3-dione hydrochloride

To a solution of 2-methoxy-2,8-diazaspiro[4,5]decane-1,3-dione hydrochloride (1.5 g) in dimethylformamide (100 ml) were added triethylamine (1 ml), 4-(tert-butyloxycarbonylamino)butyric acid (2.03 g), N-hydroxybenztriazole (1.35 g) and dicylohexylcarbodiimide (2.06 g) in sequential additions, and this was followed by stirring at room temperature for 5 hours. The resulting precipitates were then removed. The solvent was evaporated under reduced pressure, and the resulting residual oily substance was dissolved in dichloromethane (50 ml), after which it was washed with a 10% aqueous solution of citric acid and then with water. The organic layer was then dried with anhydrous magnesium sulfate, and this was followed by the evaporation of the solvent under reduced pressure. The resulting residual oil was separated by silica gel column chromatography (eluent; chloroform-acetone-methanol = 10:3:2 (v/v)). To the resulting oily substance containing the desired product was added a solution of 6N hydrogen chloride in ethanol (20 ml), and it was kept standing at room temperature for 10 minutes. The solvent was then evaporated under reduced pressure. The resulting oily substance was separated by silica gel column chromatography (eluent; chloroform-methanol-water = 14:6:1) to obtain 1.2 g of a noncrystalline solid.

Elemental analysis (as $C_{13}H_{22}ClN_3O_4$): Calculated: C, 48.83; H, 6.93; N, 13.14. Found: C, 48.91; H, 6.82; N, 13.13.

EXAMPLE 18

8-Benzyloxycarbonyl-2-dimethylamino-2,8-diazaspiro[4,5]decane-1,3-dione

To a solution of (1-benzyloxycarbonyl-4-carboxypiperidin-4-yl)acetic acid (1.28 g) in dimethylformamide (10 ml) was added dicyclohexylcarbodiimide (0.82 g), and this was followed by 30 minutes of stirring at room temperature. 1,1-Dimethylhydrazine (0.62 ml) was then added, and this was also followed by 30 minutes of stirring at room temperature. The solvent was then evaporated under reduced pressure. To the resulting residual oily compound were added acetic anhydride (10 ml) and then anhydrous sodium acetate (0.33 g), and this was followed by stirring at 100° C. for 30 minutes. The solvents were then evaporated under reduced pressure. The resulting residual substance was dissolved in ethyl acetate (50 ml), and it was washed with a saturated aqueous solution of sodium hydrogen-carbonate and then with water. The organic layer was then dried with anhydrous magnesium sulfate and the solvent was then evaporated under reduced pressure to yield an oily substance. This oily substance was separated by silica gel column chromatography (eluent; methanol-dichloromethane = 1:19 (v/v)), and the solvent for the solution containing the desired product was evaporated to obtain 0.71 g of a colorless oil.

Elemental analysis (as $C_{18}H_{23}N_3O_4$): Calculated: C, 62.59; H 6.71; N, 12.17 Found: C, 62.32; H, 6.82; N, 12.06.

EXAMPLE 19

2-Dimethylamino-2,8-diazaspiro[4,5]decane-1,3-dione hydrochloride

To the 8-benzyloxycarbonyl-2-dimethylamino-2,8-diazaspiro[4,5]decane-1,3-dione (0.4 g) which was obtained in Example 18 was added 6N hydrochloric acid (20 ml), and was followed by heating at 100° C. for 3 hours. The solvent was then evaporated; the resulting residual solid was recrystallized from ethanol-ethyl acetate to obtain 0.3 g of a colorless crystal having a melting point of from 257° to 260° C.

Elemental analysis (as $C_{10}H_{18}ClN_3O_2$): Calculated: C, 48.49; H, 7.32; N, 16.96 Found: C, 48.50; H, 7.53; N, 16.66.

EXAMPLE 20

8-Acetyl-2-methoxy-2,8-diazaspriro[4,5]decane-1,3-dione

To a solution of 2-methoxy-2,8-diazaspiro[4,5]decane-1,3-dione hydrochloride (2.35 g) in dimethylformamide (200 ml) were added triethylamine (2.8 ml) and then acetic anhydride (0.95 ml). The mixture was stirred at room temperature for 12 hours, and then solvent was evaporated off under reduced pressure. To the resulting oily substance, dichloromethane (50 ml) was added and the mixture was washed with 1N hydrochloric acid and water. The organic layer was dried over anhydrous magnesium sulfate. The solvent was evaporated off under reduced pressure. The resulting solid was recrystallized from ethanol-ethyl ether to obtain 1.1 g of colorless crystals having a melting point of from 153° to 157° C., which is the same compound obtained in Example 14.

Elemental Analysis (as $C_{11}H_{16}N_2O_4$): Calculated: C, 54.99; H, 6.71; N, 11.66 Found: C, 54.90; H, 6.82; N, 11.63.

EXAMPLE 21

2-Methoxy-8-methyl-2,8-diazaspiro[4,5]decane-1,3-dione-8-oxide hydrochloride 2-Methoxy-8-methyl-2,8-diazaspiro[4,5]decane-1,3-dione hydrochloride (0.74 g) which was synthesized in accordance with Example 1 was suspended in chloroform (20 ml). To this suspension sodium hydride (60% in oil) (0.12 g) was added, and this was followed by stirring at room temperature for 1 hour. A solution of meta-chloroperbenzoic acid (1.86 g) in chloroform (40 ml) was then added dropwise, and this was also followed by stirring at room temperature for 20 hours. The solvent was evaporated under reduced pressure; the resulting residual oily compound was separated by silica gel column chromatography (eluent; chloroform→methanol); the resulting oily compound was dissolved in methanol (30 ml), and a solution of 2N hydrogen chloride in dioxane (2 ml) was added thereto; the solvent was then evaporated under reduced pressure to yield a solid substance, which was then suspended in ethanol and filtered to obtain 0.4 g of a colorless crystal having a melting point of from 215° to 225° C. (decomposed).

Elemental analysis (as $C_{10}H_{17}ClN_2O_4$): Calculated: C, 45.37; H, 6.47; N, 10.58 Found: C, 45.10; H, 6.55; N, 10.36.

EXAMPLE 22

8-(2-Bromoethoxycarbonyl)-2-methoxy-2,8-diazaspiro[4,5]decane-1,3-dione

To a solution of 2-bromoethanol (0.81 ml) and p-nitrophenyl chloroformate (2 g) in ether (25 ml) was added dropwise, under ice-cooling, pyridine (0.71 ml). The mixture was stirred at room temperature overnight. Precipitates was filtered off, and the filtrate was washed with 1N hydrochloric acid and water, successively, followed by drying over anhydrous sodium sulfate. The solvent was evaporated off under reduced pressure to obtain 2.1 g of an oily substance.

In 16 ml of dimethylformamide was suspended 1.9 g of 2-methoxy-2,8-diazaspiro[4,5]decane-1,3-dione-hydrochloride which was obtained in Example 9. To this suspension was added 0.43 g of sodium hydride, and the mixture was stirred at 60° C. for 30 minutes, to which was then added, under ice-cooling, 2.1 g of the oily compound obtained above, followed by stirring for 2 hours at room temperature. To the mixture was then added 100 ml of water, which was stirred and subjected to extraction with dichloromethane. The dichloromethane solution was dried over anhydrous sodium sulfate, followed by evaporation of the solvent under reduced pressure. The residual oily compound was subjected to a silica gel column chromatography (eluent; dichloromethane:ethyl acetate=20:1 (V/V)). From the solution containing the desired product was evaporated off the solvent. The residual solid was recrystallized from ethyl ether to obtain 2.65 g of colorless crystals, m.p. 134° C. This compound is identical with Compound No. 5 in Table 4 of Example 15.

Elemental analysis (as $C_{12}H_{17}BrN_2O_5$): Calculated: C, 41.28; H, 4.91; N, 8.02 Found: C, 41.51; H, 4.95; N, 7.98.

EXAMPLE 23

The compounds listed in Table 5 were obtained in the same manner as in Example 22.

TABLE 5

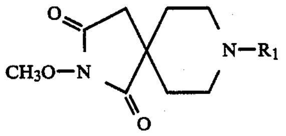

| Compound Number | $R_1$ | Melting Point (°C.) | Molecular Formula | Elemental Analysis Calculated (Found) C | H | N |
|---|---|---|---|---|---|---|
| 1 | O<br>‖<br>$-COCH_2CH_2CH_2Br$ | 129–133 | $C_{13}H_{19}BrN_2O_5$ | 42.99<br>(43.01) | 5.27<br>(5.30) | 7.71<br>(7.83) |
| 2 | O CH₃ over ‖ ∣<br>$-COCHCH_2Br$ | 101–103 | $C_{13}H_{19}BrN_2O_5$ | 42.99<br>(43.28) | 5.27<br>(5.29) | 7.71<br>(7.99) |
| 3 | O $CH_3$<br>‖ ∣<br>$-COCH_2CHBr$ | 122–125 | $C_{13}H_{19}BrN_2O_5$ | 42.99<br>(43.11) | 5.27<br>(5.17) | 7.71<br>(7.96) |
| 4 | 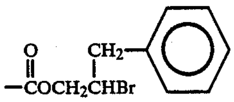 | 118–119 | $C_{19}H_{23}BrN_2O_5$ | 51.95<br>(51.76) | 5.28<br>(5.14) | 6.38<br>(6.69) |
| 5 | O $CH_2CH_3$<br>‖ ∣<br>$-COCHCH_2Br$ | 91–94 | $C_{14}H_{21}BrN_2O_5$ | 44.58<br>(44.63) | 5.61<br>(5.55) | 7.43<br>(7.59) |
| 6 | O $CH_2CH_3$<br>‖ ∣<br>$-COCH_2CHBr$ | 93 | $C_{14}H_{21}BrN_2O_5$ | 44.58<br>(44.75) | 5.61<br>(5.53) | 7.43<br>(7.50) |

TABLE 5-continued

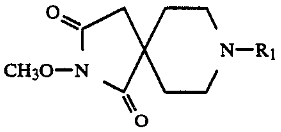

| Compound Number | $R_1$ | Melting Point (°C.) | Molecular Formula | Elemental Analysis Calculated (Found) C | H | N |
|---|---|---|---|---|---|---|
| 7 | $-\overset{\overset{O}{\|}}{C}O\overset{\overset{CH_3}{\|}}{C}H-\overset{\overset{CH_3}{\|}}{C}H-Br$ | 113–116 | $C_{14}H_{21}BrN_2O_5$ | 44.58 (44.69) | 5.61 (5.59) | 7.43 (7.72) |
| 8 | 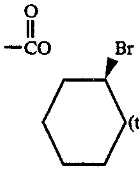 (trans-form) | 163–166 | $C_{16}H_{23}BrN_2O_5$ | 47.65 (47.85) | 5.75 (5.73) | 6.95 (6.99) |
| 9 | $-\overset{\overset{O}{\|}}{C}OCH(CH_2Br)_2$ | 107–108 | $C_{13}H_{18}Br_2N_2O_5$ | 35.32 (35.51) | 4.10 (4.00) | 6.34 (6.37) |
| 10 | $-\overset{\overset{O}{\|}}{C}OCH_2\overset{\overset{Br}{\|}}{C}HCH_2Br$ | 88–90 | $C_{13}H_{18}Br_2N_2O_5$ | 35.32 (35.46) | 4.10 (4.02) | 6.34 (6.48) |
| 11 | $-\overset{\overset{O}{\|}}{C}OCH_2CH_2F$ | 122–124 | $C_{12}H_{17}FN_2O_5$ | 50.00 (50.22) | 5.94 (5.74) | 9.72 (9.72) |
| 12 | $-\overset{\overset{O}{\|}}{C}OCH_2CH_2Cl$ | 87–90 | $C_{12}H_{17}ClN_2O_5$ | 47.30 (47.55) | 5.62 (5.32) | 9.19 (9.37) |
| 13 | $-\overset{\overset{O}{\|}}{C}OCH_2CH_2I$ | 127–130 | $C_{12}H_{17}IN_2O_5$ | 36.38 (36.56) | 4.33 (4.16) | 7.07 (7.19) |
| 14 | 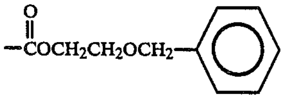 | 111–112 | $C_{19}H_{24}N_2O_6$ | 60.63 (60.56) | 6.43 (6.41) | 7.44 (7.33) |
| 15 | $-\overset{\overset{O}{\|}}{C}OCH_2CH_2N(CH_3)_2$ (hydrochloride) | oil | $C_{14}H_{24}ClN_3O_5$ | 48.07 (48.01) | 6.91 (6.83) | 12.01 (11.96) |
| 16 | 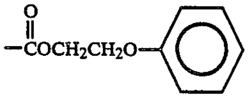 | oil | $C_{18}H_{22}N_2O_6$ | 59.66 (59.38) | 6.12 (6.02) | 7.73 (7.69) |
| 17 | $-\overset{\overset{O}{\|}}{C}OCH_2CH_2O^tBu$ | 76–78 | $C_{16}H_{26}N_2O_6$ | 56.13 (56.34) | 7.65 (7.53) | 8.18 (8.12) |
| 18 | $-\overset{\overset{O}{\|}}{C}OCH_2CH_2C{\equiv}CH$ | 111–113 | $C_{14}H_{18}N_2O_5$ | 57.14 (56.91) | 6.16 (6.13) | 9.52 (9.36) |
| 19 | $-\overset{\overset{O}{\|}}{C}OCH_2CH_2SCH_3$ | 87–90 | $C_{13}H_{20}N_2O_5S$ | 49.35 (49.53) | 6.37 (6.11) | 8.85 (9.03) |
| 20 | $-\overset{\overset{O}{\|}}{C}OCH_2CF_3$ | 75–77 | $C_{12}H_{15}F_3N_2O_5$ | 44.45 (44.66) | 4.66 (4.66) | 8.64 (8.92) |
| 21 | $-\overset{\overset{O}{\|}}{C}OCH_2CH_2CN$ | 115–117 | $C_{13}H_{17}N_3O_5$ | 52.88 (52.94) | 5.80 (57.71) | 14.23 (14.03) |

TABLE 5-continued

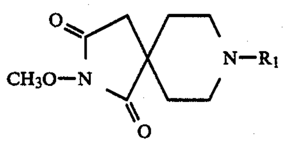

| Compound Number | $R_1$ | Melting Point (°C.) | Molecular Formula | Elemental Analysis Calculated (Found) C | H | N |
|---|---|---|---|---|---|---|
| 22 | 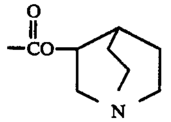 | 227–232 | $C_{17}H_{25}N_3O_5$ | 58.11 (57.94) | 7.17 (7.07) | 11.96 (11.88) |

EXAMPLE 24

2-Methoxy-8-nicotinoyl-2,8-diazaspiro[4,5]decane-1,3-dione

A solution of 2-methoxy-2,8-diazaspiro[4,5]decane-1,3-dione-hydrochloride (2.35 g) which was obtained in Example 9 and nicotinoyl chloride-hydrochloride (1.8 g) in pyridine (20 ml) was stirred for one hour at 85° C. The reaction mixture was cooled, to which was added 100 ml of an aqueous solution saturated with sodium hydrogen-carbonate, followed by extraction with dichloromethane. The dichloromethane solution was dried over anhydrous sodium sulfate, then the solvent was evaporated off. The residual solid compound was recrystallized from ethyl ether to obtain 2.35 g of colorless crystals, m.p. 199° to 201° C.

Elemental analysis (as $C_{15}H_{17}N_3O_4$): Calculated: C, 59.40; H, 5.65; N, 13.85 Found: C, 59.19; H, 5.66; N, 13.85.

EXAMPLE 25

2-Methoxy-8-(1-methylpyrimidinium-3-carbonyl)-2,8-diazaspiro[4,5]decane iodide To a solution of 2-methoxy-8-nicotinoyl-2,8-diazaspiro[4,5]decane-1,3-dione (0.75 g) which was obtained in Example 24 in methanol (10 ml) was added methyl iodide (2 ml). The mixture was stirred for 18 hours at 40° C. The solvent was evaporated off under reduced pressure, and the residual solid was recrystallized from methanol to obtain 1 g of yellow crystals, m.p. 224° to 228° C.

Elemental analysis (as $C_{16}H_{20}1N_3O_4$): Calculated: C, 43.16; H, 4.53; N, 9.44 Found: C, 42.99; H, 4.52; N, 9.54.

EXAMPLE 26

2-Methoxy-8-(1-methyl-1,4-dihydropyridine-3-carbonyl)-2,8-diazaspiro[4,5]decane-1,3-dione 2-Methoxy-8-(1-methylpyridinium-3-carbonyl)-2,8-diazaspiro[4,5]decane-1,3-dione diiodide (0.89 g) which was obtained in Example 25 was added to a mixture solvent consisting of a solution of sodium hydrosulfite (1.74 g) and sodiumcarbonate (1.6 g) in dichloromethane (30 ml) and water (30 ml). The mixture was stirred vigorously for 20 minutes at room temperature. The dichloromethane layer was separated, and the aqueous layer was then extracted with dichloromethane. Dichloromethane layers were combined and washed with water, followed by evaporating off the solvent under reduced pressure to obtain 0.5 g of yellow powder, m.p. 46° to 62° C.

Elemental analysis (as $C_{16}H_{21}N_3O_4$): Calculated: C, 60.18; H, 6.63; N, 13.16 Found: C, 59.92; H, 6.54; N, 12.99.

EXAMPLE 27

2-Methoxy-8-(1-benzylpyridinium-3-carbonyl)-2,8-diazaspiro[4,5]decane-1,3-dione bromide The yellow powdery product, m.p. 130° to 149° C., was obtained in the same manner as in Example 25.

Elemental analysis (as $C_{22}H_{24}BrN_3O_4$): Calculated: C, 55.71; H, 5.10; N, 8.86 Found: C, 55.54; H, 5.01; N, 8.66.

EXAMPLE 28

2-Methoxy-8-(1-benzyl-1,4-dihydropyridine-3-carbonyl)-2.8-diazaspiro[4,5]decane-1,3-dione Using 2-methoxy-8-(1-benzylpyridinium-3-carbonyl)-2,8-diazaspiro[4,5]decane-1,3-dione bromide which was obtained in Example 27, yellow powder, m.p. 57° to 73° C. was obtained in the same manner as in Example 26.

Elemental analysis (as $C_{22}H_{25}N_3O_4$): Calculated: C, 66.82; H, 6.37; N, 10.63 Found: C, 66.53; H, 6.21; N, 10.33.

EXAMPLE 29

3-Carbamoyl-1-[2-[(1,3-dioxo-2-methoxy-2,8-diazaspiro-[4,5]decan-8-yl)carbonyl]ethyl]pyridinium bromide 2-Methoxy-2,8-diazaspiro[4,5]decane-1,3-dione.hydrochloride (1.5 g) which was obtained in Example 9 was suspended in dimethylformamide (30 ml). To this suspension was added sodium hydride (0.16 g), and the mixture was stirred for 30 minutes at 55° C., to which was added dropwise, under ice-cooling, 3-bromopropionyl chloride (1.2 g), followed by stirring for 2 hours at room temperature. To the reaction mixture was added water (100 ml), which was subjected to extraction with dichloromethane. The dichloromethane solution was washed with 1N hydrochloric acid and water, successively, which was then dried over anhydrous sodium sulfate, followed by evaporating off the solvent under reduced pressure to obtain 1.92 g of yellowish brown oily product. A solution of 1.92 g of this oily product and 0.7 g of nicotinamide in 10 ml of ethanol was heated under reflux for 12 hours. The solvent was then evaporated off under reduced pressure. To the residual oily product were added water (50 ml) and dichloromethane (50 ml). The aqueous layer was separated and washed with dichloromethane. Water was evaporated off under reduced pressure, and the residual solid was recrystallized from ethanol to obtain 1.4 g of colorless crystals, m.p. 234° to 236° C.

Elemental analysis (as $C_{18}H_{23}BrN_4O_5$): Calculated: C, 47.48; H, 5.09; N, 12.31 Found: C, 47.50; H, 5.08; N, 12.60.

EXAMPLE 30

3-Carbamoyl-1-[2-[(1,3-dioxo-2-methoxy-2,8-diazaspiro[4,5]decane-8-yl)carbonyl]ethyl]-1,4-dihydropyridine Using 3-carbamoyl-1-[2-[(1,3-dioxo-2-methoxy-2,8-diazaspiro[4,5]decan-8-yl)carbonyl]ethyl]pyridinium bromide obtained in Example 29, yellow powder, m.p. 64° to 80° C. was obtained in the same manner as in Example 26.

Elemental analysis (as $C_{18}H_{24}N_4O_5$): Calculated: C, 57.44; H, 6.43; N, 14.88 Found: C, 57.24; H, 6.28; N, 14.59.

EXAMPLE 31

8-[1,4-Dihydro-2,6-dimethyl-5methoxycarbonyl-4-(3-nitrophenyl)pyridine-3-carbonyl]-2-methoxy-2,8-diazaspiro[4,5]decane-1,3-dione To a solution of of 2-methoxy-2,8-diazaspiro[4,5]decane-1,3-dione.hydrochloride (0.21 g) obtained in Example 9, 1,4-dihydro-2,6-dimethyl-5-methoxycarbonyl-4-(3-nitrophenyl)pyridine-3-carboxylic acid (0.3 g) and triethylamine (0.26 ml) in dimethylformamide (7 ml) was added dropwise, under ice-cooling, 0.22 ml of diethyl cyano phosphate, and the mixture was stirred for 30 minutes. To the reaction mixture was added water (20 ml), which was stirred at room temperature, followed by extraction with dichloromethane. The dichloromethane solution was dried over anhydrous sodium sulfate. The solvent was then evaporated off under reduced pressure. The residual oily product was subjected to a silica gel column chromatography (eluent, ethyl acetate), and the solvent for the solution containing the desired product was evaporated off under reduced pressure. The residual solid was recrystallized from ethanol to obtain 0.31 g of yellow crystals, m.p. 228° to 230° C.

Elemental analysis (as $C_{25}H_{28}N_4O_8$): Calculated: C, 58.59; H, 5.51; N, 10.93 Found: C, 58.54; H, 5.53; N, 10.93.

EXAMPLE 32

8-[1,4-Dihydro-2,6-dimethyl-3-nitro-4-(2-trifluoromethylphenyl)pyridine-5-carbonyl]-2-methoxy-2,8-diazaspiro[4,5]decane-1,3-dione Using 1,4-dihydro-2,6-dimethyl-3-nitro-4-(2-trifluoromethylphenyl)pyridine-5-carboxylic acid, yellow crystals, m.p. 261° to 263° C. were obtained in the same manner as in Example 31.

Elemental analysis (as $C_{24}H_{25}F_3N_4O_6$): Calculated: C, 55.17; H, 4.82; N, 10.72 Found: C, 54.94; H, 4.93; N, 10.45.

EXAMPLE 33

1,4-Dihydro-2,6-dimethyl-5-[[2-[(1,3-dioxo-2-methoxy-2,8-diazaspiro[4,5]decan-8-yl)carbonyloxy]ethyl-]aminocarbonyl]-3-methoxycarbonyl-4-(3-nitrophenyl)-pyridine (1) Using 1,4-dihydro-2,6-dimethyl-5-methoxycarbonyl-4-(3-nitrophenyl)pyridine-3-carboxylic acid (1 g) and 2-aminoethanol (0.2 g), by a similar manner to Example 31 yellow powder (0.85 g), m.p. 64° to 70° C., 1,4-dihydro-2,6-dimethyl-5-[(2-hydroxyethyl)-aminocarbonyl]-3-methoxycarbonyl-4-(3-nitrophenyl)pyridine was obtained.

Elemental analysis (as $C_{18}H_{21}N_3O_6$): Calculated: C, 57.59; H, 5.64; N, 11.19 Found: C, 57.33; H, 5.39; N, 10.92.

(2) Using 1,4-dihydro-2,6-dimethyl-5-[(2-hydroxyethyl-)aminocarbonyl]-3-methoxycarbonyl-4-(3-nitrophenyl)pyridine, yellow powder, m.p. 107° to 113° C. was obtained in the same manner as in Example 22.

Elemental analysis (as $C_{28}H_{33}N_5O_{10}$): Calculated: C, 56.09; H, 5.55; N, 11.68 Found: C, 55.97; H, 5.41; N, 11.44.

EXAMPLE 34

8-[(2-Hydroxybenzoyl)aminomethyl]-2-methoxy-2,8-diazaspiro[4,5]decane-1,3-dione

A suspension of 2-methoxy-2,8-diazaspiro[4,5]decane-1,3-dione.hydrochloride (0.55 g), salicylamide (0.32 g), p-formaldehyde (0.11 g) and triethylamine (2 ml) in ethanol (20 ml) was stirred for 15 hours at room temperature. Then, the solvent was evaporated off under reduced pressure, and the residual oily product was subjected to a silica gel column chromatography (eluent; ethyl acetate), and the solvent for the solution containing the desired product was evaporated off under reduced pressure. The residual solid was recrystallized from ethyl ether to obtain 0.52 g of colorless crystals, m.p. 96° to 99° C.

Elemental analysis (as $C_{17}H_{21}N_3O_5$): Calculated: C, 58.78; H, 6.09; N, 12.10 Found: C, 58.56; H, 6.26; N, 11.93.

EXAMPLE 35

8-[(3-Pyridyl)carbonylaminoethyl]-2-methoxy-2,8-diazaspiro[4,5]decane-1,3-dione

Using nicotinamide, reaction was conducted in the same manner as in Example 34 to obtain colorless powder, m.p. 112° to 119° C.

Elemental analysis (as $C_{16}H_{20}N_4O_4$): Calculated: C, 57.82; H, 6.07; N, 16.86 Found: C, 57.59; H, 6.08; N, 16.61.

EXAMPLE 36

8-Methyl-2-methylamino-2,8-diazaspiro[4,5]decane-1,3-dione.hydrochloride

In dimethylformamide (30 ml) was dissolved (1-methyl-4-carboxypiperidin-4-yl)acetic acid.hydrochloride (1.9g). To the solution was added dicyclohexylcarbodiimide (1.82 g), and the mixture was stirred for one hour, to which was added methylhydrazine (0.43 ml). The mixture was stirred at 60° C. for one full day. Precipitates were removed, and the solvent was evaporated off under reduced pressure. The residual oily product was subjected to a silica gel column chromatography [eluent; n-butanol:acetic acid:methanol:water = 1:1:1:1

(V/V)]. To the solution containing the desired product was added 4 ml of 1N hydrochloric acid. Then, the solvent was evaporated off, and the residual solid product was recrystallized from ethanol to obtain 0.25 g of colorless solid, m.p. 235° to 260° C.

Elemental analysis (as $C_{10}H_{18}ClN_3O_2$): Calculated: C, 48.19; H, 7.32; N, 16.96 Found: C, 47.95; H, 7.47; N, 16.83.

EXAMPLE 37

8-Benzyl-2-benzyloxy-2,8-diazaspiro[4,5]decane-1,3-dione

To a solution of (1-benzyl-4-carboxypiperidin-4-yl)acetic acid.hydrochloride (31.3 g) in dimethylformamide (200 ml) was added dicyclohexylcarbodiimide (20.6 g). The mixture was stirred for one hour at room temperature, to which were added benzyloxyamine hydrochloride (16 g) and triethylamine (14 ml). The mixture was stirred for further one hour at room temperature, followed by evaporating off the solvent under reduced pressure. To the residue were added acetic anhydride (150 ml) and sodium acetic anhydride (21 g). The mixture was stirred for one hour at 100° C., then insolubles were filtered off, and the solvent was evaporated off under reduced pressure. To the residue was added ethyl acetate (200 ml), to which was further added a saturated aqueous solution of sodium hydrogencarbonate until the aqueous layer became alkaline. The organic layer was washed with water, dried over anhydrous magnesium sulfate, followed by evaporating off the solvent under reduced pressure. To the residual oil was added 100 ml of acetonitrile, and insolubles were filtered off. Acetonitrile was evaporated off, and the residue was recrystallized from acetonitrile-ethyl ether to obtain 16.5 g of a colorless solid, m.p. 146° to 152° C.

Elemental analysis (as $C_{22}H_{24}N_2O_3$): Calculated: C, 72.51; H, 6.64; N, 7.69 Found: C, 72.28; H, 6.60; N, 7.57.

EXAMPLE 38

2-Hydroxy-2,8-diazaspiro[4,5]decane-1,3-dione.hydrochloride

In a mixture solvent consisting of methanol (100 ml) and 1N hydrochloric acid (50 ml) was dissolved 8-benzyl-2-benzyloxy-2,8-diazaspiro[4,5]decane-1,3-dione hydrochloride (16.0 g). The solution was subjected to catalytic reduction at 40° C. for 12 hours under atmospheric pressure, using palladium as the catalyst. After the reaction, the catalyst was removed, and the solvent was evaporated off under reduced pressure. The residual solid was recrystallized from ethanol to obtain 8.9 g of a colorless solid, m.p. 250° to 277° C.

Elemental analysis (as $C_8H_{13}ClN_2O_3$): Calculated: C, 43.55; H, 5.94; N, 12.70 Found: C, 43.59; H, 5.97; N, 12.66.

EXAMPLE 39

8-tert-Butyloxycarbonyl-2-hydroxy-2,8-diazaspiro[4,5]-decane-1,3-dione

In a mixture solvent consisting of water (50 ml) and dioxane (50 ml) was dissolved 2-hydroxy-2,8-diazaspiro[4,5]decane-1,3-dione.hydrochloride (8.35 g). To the solution were added triethylamine (14 ml) and 2-(tert. butyloxycarbonylthio)-4,6-dimethylpyrimidine (9.6 g). The mixture was stirred for 2 hours at room temperature. The solvent was evaporated off under reduced pressure, and the residual oil was evaporated in 100 ml of ethyl acetate. To the solution was added 100 ml of a saturated aqueous solution of sodium hydrogencarbonate. The aqueous layer was made acid with a solid citric acid, followed by extraction with 100 ml of ethyl acetate. The organic layer was washed with 50 ml of 1N hydrochloric acid and water, which was then dried over anhydrous magnesium sulfate, followed by evaporating off the solvent to leave an oil. This oil was solidified with diethyl ether-n-hexane, which was collected by filtration to obtain 9.6 g of a colorless solid, m.p. 151° to 154° C.

Elemental analysis (as $C_{13}H_{20}N_2O_5$): Calculated: C, 54.92; H, 7.09; N, 9.85 Found: C, 54.90; H, 7.17; N, 9.67.

EXAMPLE 40

8-tert-Butyloxycarbonyl-2-cyanomethyloxy-2,8-diazaspiro[4,5]decane-1,3-dione To a solution of 8-tert-butyloxycarbonyl-2-hydroxy-2,8-diazaspiro[4,5]decane-1,3-dione (0.56 g) in dimethylformamide (5 ml) was added 88 mg of sodium hydride (60% in oil), and the mixture was stirred for one hour at room temperature. To the mixture was added chloroacetonitrile (140 μl). The whole mixture was stirred for 2 hours at room temperature, to which was added ethyl acetate (30 ml), followed by washing with a saturated aqueous solution of sodium hydrogencarbonate and then with a 10% aqueous solution of citric acid. The organic layer was dried over anhydrous magnesium sulfate, then the solvent was evaporated off. The residue was recrystallized from ethyl acetate-diethyl ether to obtain 0.53 g of a colorless solid, m.p. 138° to 139° C.

Elemental analysis (as $C_{15}H_{21}N_3O_5$): Calculated: C, 55.72; H, 6.55; N, 13.00 Found: C, 55.60; H, 6.56; N, 12.98.

EXAMPLE 41

8-Benzyloxycarbonyl-2-benzyloxycarbonyloxy-2,8-diazaspiro[4,5]decane-1,3-dione To a solution of 2-hydroxy-2,8-diazaspiro-[4,5]decane-1,3-dione.hydrochloride (3.3 g) were added sodium hydrogencarbonate (2.43 g) and benzyloxycarbonyl chloride (3.2 ml). The mixture was stirred for 3 hours at room temperature, which was extracted with ethyl acetate (100 ml). The organic layer was dried over anydrous magnesium sulfate, then the solvent was evaporated off. The residual solid was recrystallized from diethyl ether-n-hexane to obtain 6.0 g of a colorless solid, m.p. 114° C.

Elemental analysis (as $C_{24}H_{24}N_2O_7$): Calculated: C, 63.71; H, 5.35; N, 6.19 Found: C, 63.72; H, 5.37; N, 6.21.

EXAMPLE 42

8-Benzyloxycarbonyl-2-hydroxy-2,8-diazaspiro-[4,5]decane-1,3-dione

To a solution of 8-benzyloxycarbonyl-2-benzyloxycarbonyloxy-2,8-diazaspiro[4,5]decane-1,3-dione (5.6 g) in dichloromethane (50 ml) was added N,N-dimethyl-1,3-propanediamine (1.9 ml), and the mixture was stirred overnight at room temperature, to which was then added 1N hydrochloric acid (50 ml). The organic layer was washed with water, dried over anhydrous magnesium sulfate. The solvent was then evaporated off. The residual solid was recrystallized from ethyl ether-n-hexane to obtain 3.8 g of a colorless solid, m.p. 131° to 132° C.

Elemental analysis (as $C_{16}H_{18}N_2O_5$): Calculated: C, 60.37; H, 5.70; N, 8.80 Found: C, 60.42; H, 5.79; N, 8.65.

EXAMPLE 43

8-Benzyloxycarbonyl-2-cyanomethyloxy-2,8-diazaspiro[4,5]decane-1,3-dione

To a solution of 8-benzyloxycarbonyl-2-hydroxy-2,8-diazaspiro[4,5]decane-1,3-dione (0.96 g) in dimethylformamide (5 ml) was added 132 mg of sodium hydride (60% in oil), and the mixture was stirred for one hour at room temperature. To the reaction mixture was added 210 μl of chloroacetonitrile, and the mixture was stirred for 2 hours at room temperature. The reaction mixture was treated in the same manner as in Example 40 to obtain 1.0 g of a non-crystalline solid.

Elemental analysis (as $C_{18}H_{19}N_3O_5$): Calculated: C, 60.50; H, 5.36; N, 11.76 Found: C, 60.53; H, 5.47; N, 11.67.

EXAMPLE 44

2-Cyanomethyloxy-2,8-diazaspiro[4,5]decane-1,3-dione

In a mixture solvent consisting of methanol (10 ml) and dimethylformamide (10 ml) was dissolved 8-benzyloxycarbonyl-2-cyanomethyl-2,8-diazaspiro[4,5]decane-1,3-dione (0.6 g). The solution was subjected to catalytic hydrogenation for 5 hours at room temperature and under atmospheric pressure, using palladium as the catalyst. The catalyst was removed, and the solvent was evaporated off, then, the residual solid was recrystallized from ethanol to obtain 0.38 g of a coloress solid, m.p. 273° to 278° C.

Elemental analysis (as $C_{10}H_{13}N_3O_3$): Calculated: C, 53.80; H, 5.87; N, 18.22 Found: C, 53.81; H, 5.92; N, 18.80.

EXAMPLE 45

8-tert-Butyloxycarbonyl-2-[2-(hydroxy)ethyloxy]-2,8-diazaspiro[4,5]decane-1,3-dione Employing 8-tert-butyloxycarbonyl-2-hydroxy-2,8-diazaspiro[4,5]decane-1,3-dione (0.56 g) and 2-bromoethanol (210 μl), reaction was conducted in the same manner as in Example 40 to obtain 0.40 g of a coloress solid, m.p. 97° to 98° C.

Elemental analysis (as $C_{15}H_{24}N_2O_6$): Calculated: C, 54.87; H, 7.37; N, 8.53 Found: C, 54.67; H, 7.56; N, 8.28.

EXAMPLE 46

2-[2-(Hydroxy)ethyloxy]-2,8-diazaspiro[4,5]decane-1,3-dione.hydrochloride

To 8-tert-butyloxycarbonyl-2-(2-hydroxy)ethyloxy-2,8-diazaspiro[4,5]decane-1,3-dione (0.72 g) was added trifluoroacetic acid (2 ml), and the mixture was left standing at room temperature for 10 minutes. To the mixture was added ethanol (20 ml), to which was further added 1 ml of an ethanol solution of 3.6N hydrogen chloride. The solvent was then evaporated off, and the residue was recrystallized from ethanol to give 0.57 g of a colorless solid, m.p. 115° to 123° C.

Elemental analysis (as $C_{10}H_{17}ClN_2O_4$): Calculated: C, 45.37; H, 6.47; N, 10.58 Found: C, 45.67; H, 6.21; H, 10.41.

EXAMPLE 47

8-Benzyloxycarbonyl-2-nitromethyloxy-2,8-diazaspiro[4,5]decane-1,3-dione

Employing 8-benzyloxycarbonyl-2-hydroxy-2,8-diazaspiro[4,5]decane-1,3-dione (0.64 g) and bromonitromethane (140 μl), reaction was conducted in the same manner as in Example 40 to obtain 0.25 g of a colorless solid, m.p. 137° to 139° C.

Elemental analysis (as $C_{17}H_{19}N_3O_7$): Calculated: C, 54.11; H, 5.08; N, 11.13 Found: C, 54.24; H, 5.13; N, 11.24.

EXAMPLE 48

8-tert-Butyloxycarbonyl-2-methoxycarbonylmethyloxy-2,8-diazaspiro[4,5]decane-1,3-dione Employing 8-tert-butyloxycarbonyl-2-hydroxy-2,8-diazaspiro[4,5]decane-1,3-dione (0.56 g) and methylbromoacetate (190 μl), reaction was conducted in the same manner as in Example 40 to obtain an oily compound. This was separated by column chromatography (eluent; dichloromethane) to obtain 0.67 g of a coloress oily compound.

Elemental analysis (as $C_{18}H_{24}N_2O_7$): Calculated: C, 53.93; H, 6.79; N, 7.86 Found: C, 53.73; H, 6.89; H, 7.82.

EXAMPLE 49

2-Methoxycarbonylmethyloxy-2,8-diazaspiro[4,5]decane-1,3-dione.hydrochloride

In trifluoroacetic acid (3 ml) was dissolved 8-tert-butyloxycarbonyl-2-methoxycarbonylmethyloxy-2,8-diazaspiro[4,5]decane-1,3-dione (0.5 g), and the solution was left standing at room temperature for 10 minutes. To the solution was added methanol (20 ml), to which was added 2 ml of a methanol solution of 1N hydrogen chloride. The solvent was evaporated off under reduced pressure, and the residual oil was crystallized from ether-methanol to obtain 0.32 g of a coloress solid, m.p. 174° to 178° C.

Elemental analysis (as $C_{11}H_{17}ClN_2O_5$): Calculated: C, 44.98; H, 5.83; N, 9.54 Found: C, 44.91; H, 5.75; N, 9.49.

EXAMPLE 50

8-Benzyloxycarbonyl-2-methoxy-2,8-diazaspiro[4,5]-decane-3-thion-1-one

To a solution of 8-benzyloxycarbonyl-2-methoxy-2,8-diazaspiro[4,5]decane-1,3-dione (2.9 g) in toluene (30 ml) was added a Lawesson reagent ([2,4-bis(4-methoxyphenyl)-1,3-dithia-2,4-diphosphethane-2,4-disulfide]) (2.38 g), and the mixture was heated for 3 hours under reflux. The solvent was then evaporated off under reduced pressure, and the residual oil was dissolved in ethyl acetate (50 ml), which was washed with water and then dried over anhydrous magnesium sulfate. The solvent was evaporated off, and the residual oil was subjected to a silica gel column chromatography [eluent; methanol:dichloromethane = 1.50 (V/V)]. The earlier eluate fraction and the later eluate fraction were separated. The solvent for the later eluate fraction was evaporated off and the residual solid was recrystallized from ethyl ether to obtain 2.1 g of a pale yellow solid, m.p. 89° to 90° C.

Elemental analysis (as $C_{17}H_{20}N_2O_4S$): Calculated: C, 58.60; H, 5.79; N, 8.04 Found: C, 58.48; H, 5.84; N, 7.97.

EXAMPLE 51

8-Benzyloxycarbonyl-2-methoxy-2,8-diazaspiro[4,5]-decane-1,3-dithione

The earlier eluate fractions in the column chromatography in Example 50 were combined, and the solvent was evaporated off. The crude crystals thus obtained was recrystallized from ethyl ether to obtain 0.5 g of a yellow solid, m.p. 127° C.

Elemental analysis (as $C_{17}H_{20}N_2O_3S_2$): Calculated: C, 56.02; H, 5.53; N, 7.68 Found: C, 55.76; H, 5.53; N, 7.61.

EXAMPLE 52

2-Methoxy-2,8-diazaspiro[4,5]decane-3-thion-1-one.hydrobromide

In an acetic acid solution (5 ml) of 25% hydrogen bromide was dissolved 8-benzyloxycarbonyl-2-methoxy-2,8-diazaspiro[4,5]decane-3-thion-1-one (0.5 g), and the solution was left standing at room temperature for 20 minutes. To the solution was added ethyl ether (100 ml), and resulting precipitates were collected by filtration, followed by recrystallization from ethanol to obtain 0.4 g of a pale yellow solid, m.p. 235° to 237° C.

Elemental analysis (as $C_9H_{15}BrN_2O_2S$): Calculated: C, 35.53; H, 5.30; N, 9.21 Found: C, 35.81; H, 5.14; N, 9.18.

EXAMPLE 53

2-Methoxy-2,8-diazaspiro[4,5]decane-1,3-dithione.hydrobromide

Employing 8-benzyloxycarbonyl-2-methoxy-2,8-diazaspiro[4,5]decane-1,3-dithione (0.36 g) obtained in Example 51, reaction was conducted in the same manner as in Example 52 to obtain 0.3 g of a yellow solid, m.p. 204' C.

Elemental analysis (as $C_9H_{15}BrN_2OS_2$): Calculated: C, 34.73; H, 4.86; N, 9.00 Found: C, 34.87; H, 4.83; N, 8.95.

Example of pharmaceutical preparation 1

(1) 2-Methoxy-2,8-diazaspiro[4,5]decane-1,3-dione hydrochloride: 10 g
(2) Lactose: 198 g
(3) Corn starch: 50 g
(4) Magnesium stearate: 2 g)

(1), (2) and 20 g of the corn starch were mixed together, and this was followed by granulation along with a paste which was prepared from 15 g of the corn starch. To the resulting granules 15 g of the corn starch and (4) were added, and the resulting mixture was compressed using a compressing tableting machine to produce 2,000 tablets having a diameter of 3 mm, containing 5 mg of (1) per tablet.

Example of pharmaceutical preparation 2

(1) 2-Methoxy-8-methyl-2,8-diazaspiro[4,5]decane-1,3-dione: 20 g
(2) Lactose: 198 g
(3) Corn starch: 40 g
(4) Magnesium stearate: 2 g (1), (2) and 15 g of the corn starch were mixed together, and this was followed by granulation along with a paste which was prepared from 15 g of the corn starch. To the resulting granules 10 g of the corn starch and (4) were added, and the resulting mixture was compressed using a compressing tableting machine to produce 2,000 tablets having a diameter of 5 mm, containing 10 mg of (1) per tablet.

Nootropic Action

Effect on $CO_2$-induced amnesia in mice

Effect of the compound (I) on inpairment of passive avoidance response, induced by exposing mice to 100% $CO_2$ gas, was evaluated. Male ICR mice (Japan Clea) aged 5 weeks were used. The experimental apparatus consisted of two chambers, in which one illuminated chamber (9×9×25 cm) was connected to a dark chamber (25×25×30 cm) with a guillotine door. Each mouse was placed in the illuminated chamber and then allowed to enter the dark one. When the mouse entered the dark chamber, the door was closed and AC 0.5 mA footshock was applied to the floor grid of the dark chamber. The mouse can memorize the experience after receiving the uncomfortable stimulus for a few weeks. Next, the consolidation processes of memory were disturbed by an experimental manipulation: Each mouse was placed under the hypoxic condition by being placed into a 4L desiccator filled with 100% $CO_2$ gas, immediately after receiving the footshock in the dark chamber. When his respiratory function was stopped, the mouse was taken out from the desiccator and given an artificial respiration till recovering spontaneous respiration. This procedure disturbed the consolidation of the memory (experience of footshock). On the next day, a retention test was performed to see whether the mouse memorized the footshock or not. In the test, the mouse was again placed in the illuminated compartment and the latency to enter the dark compartment was measured.

The mice subjected to hypoxia entered the dark compartment with short latency, 10–20 sec. The mice treated with the compound (I) showed much longer latency than the controls. The ameliorating effect of compounds on the amnesia induced by hypoxia was evaluated by the latency time, and was expressed as the percent change of the mean time of the vehicle-treated control group (Table 6.). The compounds were suspended in 5% arabic gum solution, and administered orally 30 min. before the test.

TABLE 6

| Compound Exp. No. | Dose (mg/kg, p.o.) | Anti-amnesia |
|---|---|---|
| Saline | — | 100 |
| 1 | 0.1 | 277* |
| 9 | 0.1 | 227* |
| | 0.3 | 321** |
| 22 | 1.0 | 311* |
| Reference RS-86 | 0.3 | 258* |

*P < 0.05,
**P < 0.01

RS-86

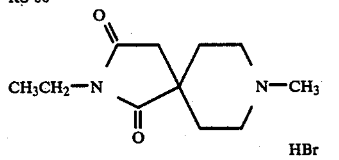

European Journal of Pharmacology, 125, 45–62(1986)

General Symptoms (Side Effects)

Four mice were used for each group. Mice were placed in stainless steel cages (13×18×25 cm) and after a 1-hr habitation period the compounds were administered. Symptoms of mice were observed for 4 hours after the compounds were administered. Peripheral and central effects of the compounds were estimated with the incidences of diarrhea, salivation and mydriasis and with the incidences of tremor and sedation and a grade of hypothermia, respectively.

The compounds which were soluble in saline were solubilized in saline and the other were suspended in 5% arabic gum solution. Each compound was administered intraperitoneally (i.p.). The results are shown in Table 7.

TABLE 7

| Compound Exp. No. | Sedation | Tremor | Hypothermia | Salivation | Diarrhea | Mydriasis |
|---|---|---|---|---|---|---|
| 1 | ++ | ++ | − | +++ | − | − |
| 9 | ++ | − | + | +++ | ++ | − |
| 22 | + | − | + | + | + | + |
| Reference RS-86 | +++ | + | +++ | +++ | +++ | ++ |

Scorings of the symptoms were made as follows.
+++: marked
++: moderate
+: mild
−: non-detected LD$_{50}$ value and Therapeutic index Ten mice were used for each group. LD$_{50}$ value and therapeutic index were estimated with the dose (mg/kg, p.o.) which induced death in 50% of mice and with a ratio of LD$_{50}$ value to a minimum effective dose (MED) for $CO_2$-induced amnesia, respectively. The results are shown in Table 8.

TABLE 8

| Compound Exp. No. | LD$_{50}$ (mg/kg, p.o.) | Anti-amnesia MED (mg/kg, p.o.) | Therapeutic Index |
|---|---|---|---|
| 9 | 2,008 | 0.1 | 20,080 |
| Reference RS-86 | 574 | 0.3 | 1,913 |

Effects of the invention

Aza-spiro compound (I) and salt thereof of the present invention show marked ameliorating effect on $CO_2$-induced amnesia in mice, and the effect was more prominent than that of RS-86. Especially, compound (I) and its salt have much weaker side effects, lower toxicity and wider therapeutic index compared with the known compound, RS-86.

The aza-spiro compound (I) and its salt may be useful for the prevention and therapy of senile dementia of Alzheimer type, vascular-type dementia and dementia derived from Alzheimer's disease, Pick's disease, Huntington's disease, Creutzfeldt-Jakob's disease, Parkinson's disease and spinocerebellar degeneration.

We claim:

1. An azaspiro compound of the formula:

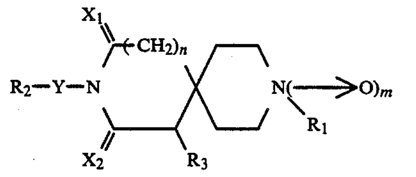

wherein $R_1$ and $R_2$ independently represent hydrogen, a hydrocarbon residue which may have a substituent, or an acyl group which may have a substituent; $R_3$ represents hydrogen or a hydrocarbon residue which may have a substituent; each of $X_1$ and $X_2$ is oxygen or sulfur; Y represents oxygen, sulfur or a group of the formula —N($R_4$)—, wherein $R_4$ represents hydrogen or a lower alkyl group; m represents 0 or 1; and n represents 0 or 1, wherein the hydrocarbon residue which may have a substituent represented by $R_1$, $R_2$ and $R_3$ is a straight-chain or branched ($C_{1-6}$) alkyl, a straight-chain or branched ($C_{2-4}$) alkenyl, a straight-chain or branched ($C_{2-4}$) alkynyl, a ($C_{3-7}$) monocyclic cycloalkyl, bicyclo[3,2,1]oct-2-yl, bicyclo[3,3,1]nonan-2-yl, phenyl or naphthyl;

the acyl group which may have a substituent represented by $R_1$ and $R_2$ is a carboxylic acyl, a carbamic acyl, a sulfonic acyl or a substituted oxycarbonyl; and the hydrocarbon residue and the acyl group may have one to three substituents selected from the group consisting of halogen, nitro, cyano, hydroxy, ($C_{1-4}$)alkoxy, ($C_{1-4}$)alkylthio, amino, mono- or di($C_{1-4}$) alkyl-substituted amino, mono- or diaralkyl-substituted amino, mono- or di-pyridylcarbonyl-substituted amino, ($C_{1-4}$) alkoxycarbonyl, hydroxycarbonyl, ($C_{1-6}$)alkylcarbonyl, ($C_{3-6}$)cycloalkylcarbonyl, carbamoyl, mono- or di($C_{1-4}$)alkyl-substituted carbamoyl, phenyl, phenoxy, benzoyl, phenoxycarbonyl, phenyl($C_{1-4}$)alkyl-carbamoyl and phenylcarbamoyl, all of the phenyl of which may have one to four substituents selected from among ($C_{1-4}$)alkyl, halogen, hydroxyl, benzyloxy, amino mono- or di-($C_{1-4}$)alkyl-substituted amino, nitro and ($C_{1-4}$)alkoxycarbonyl, or a physiologically acceptable salt of said compound.

2. A compound as claimed in claim 1, wherein the acyl group which may have a substituent represented by $R_1$ and $R_2$ is (i) a ($C_{1-6}$)alkylcarbonyl which may be substituted by amino, 3-carbamoyl-1,4-dihydropyridin-1-yl, 3-carbonyl-1-pyridyl or phenoxy;

(ii) a ($C_{3-8}$)cycloalkylcarbonyl, a ($C_{3-8}$)cycloalkyl-($C_{1-6}$)alkylcarbonyl, a ($C_{2-6}$)alkenylcarbonyl, a ($C_{2-6}$)alkynylcarbonyl, benzoyl, naphthoyl, a pyridylcarbonyl or a dehydropyridylcarbonyl each of which may be substituted by ($C_{1-4}$)alkyl, benzyl, methoxycarbonyl, 3-nitrophenyl, nitro or 2-trifluorophenyl;

(iii) a pyridiniumcarbonyl which is substituted at nitrogen by ($C_{1-4}$)alkyl;

(iv) carbamoyl or a mono- or di-substituted carbamoyl the substituent of which is ($C_{1-4}$)alkyl, ($C_{3-6}$)alkenyl, ($C_{3-6}$)alkynyl, phenyl or naphthyl;

(v) sodium sulfonyl, a ($C_{1-6}$)alkylsulfonyl, a ($C_{2-6}$)alkenylsulfonyl, a ($C_{2-6}$)alkynylsulfonyl, phenylsulfonyl or naphthalenesulfonyl;

(vi) a $(C_{1-6})$alkyloxycarbonyl which may be substituted by halogen, cyano, benzyloxy, phenoxy, di-$(C_{1-3})$alkylamino, $(C_{1-4})$alkyloxy, $(C_{1-3})$alkylthio, 4-(3-nitrophenyl)-2,6-dimethyl-3-methoxycarbonyl-1,4-dihydropyridine-5-ylcarbonylamino or dihydropyridylcarbonylamino;

(vii) a $(C_{3-8})$cycloalkyloxycarbonyl which may be substituted by halogen;

(viii) cyclopentylmethyloxycarbonyl;

(ix) a $(C_{2-7})$alkenyloxycarbonyl or a $(C_{2-7})$alkynyloxycarbonyl; or (x) phenyloxycarbonyl, benzyloxycarbonyl or phenethyloxycarbonyl each of which may be substituted by halogen, or quinuclidinyloxycarbonyl.

3. A compound as claimed in claim 1, wherein $R_3$ is hydrogen.

4. A compound as claimed in claim 1, wherein Y is oxygen.

5. A compound as claimed in claim 1, wherein m is 0.

6. A compound as claimed in claim 1, wherein $X_1$ is oxygen.

7. A compound as claimed in claim 1, wherein $X_2$ is oxygen.

8. A compound as claimed in claim 1, wherein n is 0.

9. A compound as claimed in claim 1, wherein $R_1$ is hydrogen, a $(C_{1-6})$ alkyl, $C_{1-4})$ alkyloxycarbonyl unsubstituted or substituted by halogen, or a phenyloxycarbonyl, benzyloxycarbonyl or phenethyloxycarbonyl.

10. A compound as claimed in claim 1, wherein $R_1$ is hydrogen or a $(C_{1-4})$ alkyl.

11. A compound as claimed in claim 1, wherein $R_2$ is an unsubstituted $C_{1-6})$ alkyl.

12. A compound as claimed in claim 1, wherein the compound is 2-methoxy-2,8-diazaspiro[4,5]decane-1,3-dione hydrochloride.

13. A compound as claimed in claim 1, wherein the compound is 2-methoxy-8-(2-bromoethyloxycarbonyl)-2,8-diazaspiro[4,5]decane-1,3-dione.

14. A pharmaceutical composition for treating and/or preventing dementia which comprises, as an active ingredient, an effective amount of a compound or physiologically acceptable salt thereof as defined in claim 1, and physiologically acceptable carrier or diluent therefor.

15. A method of treating and/or preventing dementia, which comprises administering an effective amount of a compound or physiologically acceptable salt thereof as defined in claim 1 to a mammal.

* * * * *